United States Patent
Lako et al.

(10) Patent No.: US 10,982,188 B2
(45) Date of Patent: Apr. 20, 2021

(54) SYNTHETIC RETINA

(71) Applicant: University of Newcastle Upon Tyne, Newcastle upon Tyne (GB)

(72) Inventors: Majlinda Lako, Newcastle upon Tyne (GB); Carla Mellough, Newcastle Upon Tyne (GB)

(73) Assignee: Newcells Biotech Limited, Newcastle upon Tyne (GB)

( * ) Notice: Subject to any disclaimer, the term of this patent is extended or adjusted under 35 U.S.C. 154(b) by 33 days.

(21) Appl. No.: 15/118,610

(22) PCT Filed: Feb. 16, 2015

(86) PCT No.: PCT/GB2015/050441
§ 371 (c)(1),
(2) Date: Aug. 12, 2016

(87) PCT Pub. No.: WO2015/121687
PCT Pub. Date: Aug. 20, 2015

(65) Prior Publication Data
US 2017/0218335 A1    Aug. 3, 2017

(30) Foreign Application Priority Data
Feb. 16, 2014 (GB) .................... 1402692

(51) Int. Cl.
| | | |
|---|---|---|
| C12N 5/079 | (2010.01) | |
| C12N 5/0793 | (2010.01) | |
| A61K 35/30 | (2015.01) | |
| A61L 27/36 | (2006.01) | |
| A61L 27/54 | (2006.01) | |
| G01N 33/50 | (2006.01) | |

(52) U.S. Cl.
CPC ............ *C12N 5/0621* (2013.01); *A61K 35/30* (2013.01); *A61L 27/3604* (2013.01); *A61L 27/3641* (2013.01); *A61L 27/3687* (2013.01); *A61L 27/54* (2013.01); *C12N 5/062* (2013.01); *G01N 33/5044* (2013.01); *C12N 2500/32* (2013.01); *C12N 2500/38* (2013.01); *C12N 2500/90* (2013.01); *C12N 2500/99* (2013.01); *C12N 2501/105* (2013.01); *C12N 2506/02* (2013.01); *C12N 2506/45* (2013.01); *C12N 2513/00* (2013.01); *C12N 2533/90* (2013.01)

(58) Field of Classification Search
CPC .................. C12N 5/0621; C12N 5/062; C12N 2501/105; C12N 2533/90; C12N 2500/99; C12N 2500/32; C12N 2500/38; C12N 2500/90; C12N 2506/02; C12N 2506/45; C12N 2513/00; A61K 35/30; A61L 27/3604; A61L 27/3641; A61L 27/3687; A61L 27/54; G01N 33/5044; A61P 27/02
See application file for complete search history.

(56) References Cited

U.S. PATENT DOCUMENTS

| | | | |
|---|---|---|---|
| 2011/0223140 A1* | 9/2011 | Park ..................... | C12N 5/0621 424/93.7 |
| 2011/0229440 A1* | 9/2011 | Dealy .................. | C12N 5/0655 424/93.7 |
| 2011/0269173 A1* | 11/2011 | Zhu ...................... | C12N 5/0621 435/29 |

FOREIGN PATENT DOCUMENTS

| | | | | |
|---|---|---|---|---|
| EP | 2 383 333 | | 11/2011 | |
| JP | 2002356440 A | * | 12/2002 | |
| WO | WO-2004081040 A2 | * | 9/2004 | .......... A61K 48/005 |
| WO | WO 2011/043591 A2 | | 4/2011 | |
| WO | WO 2011/043592 | | 4/2011 | |
| WO | WO 2012/177968 | | 12/2012 | |

OTHER PUBLICATIONS

Mellough et al. "Efficient stage-specific differentiation of human pluripotent stem cells toward retinal photoreceptor cells." Stem Cells. Apr. 2012;30(4):673-86. (Year: 2012).*
Pearson et al. "Photoreceptor replacement therapy: challenges presented by the diseased recipient retinal environnnent." Vis Neurosci. Sep. 2014;31(4-5):333-44. (Year: 2014).*
Singh et al. "Pluripotent Stem Cells for Retinal Tissue Engineering: Current Status and Future Prospects." Stem Cell Rev. Aug. 2018; 14(4):463-483. (Year: 2018).*
Osakada et al. "Toward the generation of rod and cone photoreceptors from mouse, monkey and human embryonic stem cells." Nature Biotechnology vol. 26, pp. 215-224 (2008) (Year: 2008).*
Diloreto et al., Cyclosporine treatment promotes survival of human fetal neural retina transplanted to the subretinal space of the light-damaged Fischer 344 rat. Exp Neurol. Jul. 1996;140(1):37-42.
Eiraku et al., Self-organizing optic-cup morphogenesis in three-dimensional culture. Nature. Apr. 7, 2011;472(7341):51-6. doi: 10.1038/nature09941.
Mellough et al., Efficient stage-specific differentiation of human pluripotent stem cells toward retinal photoreceptor cells. Stem Cells. Apr. 2012;30(4):673-86. doi: 10.1002/stem.1037.
Mellough et al., IGF-1 Signaling Plays an Important Role in the Formation of Three-Dimensional Laminated Neural Retina and Other Ocular Structures From Human Embryonic Stem Cells. Stem Cells. Aug. 2015;33(8):2416-30. doi: 10.1002/stem.2023. Epub May 13, 2015.

(Continued)

*Primary Examiner* — Titilayo Moloye
(74) *Attorney, Agent, or Firm* — Wolf, Greenfield & Sacks, P.C.

(57) ABSTRACT

The invention provides a method of producing a synthetic retina, comprising: i) providing a three dimensional stem cell culture throughout the differentiation time course, ii) differentiating the three dimensional stem cell culture for a first time period in a first neural cell culture medium comprising: a) L-glutamine; b) B27 supplement; and c) an IGF-1 receptor agonist, iii) subsequently differentiating the three dimensional stem cell culture for a second time period in a second neural cell culture medium comprising: a) L-glutamine; b) B27 supplement; c) N2 supplement; and d) an IGF-1 receptor agonist, wherein said synthetic retina contains laminated retinal tissue comprising.

20 Claims, 17 Drawing Sheets
Specification includes a Sequence Listing.

(56) References Cited

OTHER PUBLICATIONS

Lamba et al., Efficient generation of retinal progenitor cells from human embryonic stem cells. Proc Natl Acad Sci U S A. Aug. 22, 2006;103(34):12769-74.

Lamba et al., Generation, purification and transplantation of photoreceptors derived from human induced pluripotent stem cells. PLoS One. Jan. 20, 2010;5(1):e8763. doi: 10.1371/journal.pone.0008763.

Meyer et al., Modeling early retinal development with human embryonic and induced pluripotent stem cells. Proc Natl Acad Sci U S A. Sep. 29, 2009;106(39):16698-703. doi: 10.1073/pnas.0905245106.

Meyer et al., Optic vesicle-like structures derived from human pluripotent stem cells facilitate a customized approach to retinal disease treatment. Stem Cells. Aug. 2011;29(8):1206-18. doi: 10.1002/stem.674.

Nakano et al., Self-formation of optic cups and storable stratified neural retina from human ESCs. Cell Stem Cell. Jun. 14, 2012;10(6):771-85. doi: 10.1016/j.stem.2012.05.009.

Zhong et al., Generation of three-dimensional retinal tissue with functional photoreceptors from human iPSCs. Nat Commun. Jun. 10, 2014;5:4047. doi: 10.1038/ncomms5047.

\* cited by examiner

Figure 2. Schematic presentation of retinal histogenesis which is recapitulated during murine ESC differentiation resulting in formation of optic cup which is able to differentiate into a fully stratified neural retina and RPE.

Figure 12

>sp|P05019-2|IGF1_HUMAN Isoform 2 of Insulin-like growth factor I OS=Homo sapiens GN=IGF1

SEQ ID NO: 1

MGKISSLPTQLFKCCFCDFLKVKMHTMSSSHLFYLALCLLTFTSSATAGPETLCGAELVDA
LQFVCGDRGFYFNKPTGYGSSSRRAPQTGIVDECCFRSCDLRRLEMYCAPLKPAKSARS
VRAQRHTDMPKTQKEVHLKNASRGSAGNKNYRM

```
SEQUENCE LISTING

<160> NUMBER OF SEQ ID NOS: 1

<210> SEQ ID NO 1
<211> LENGTH: 153
<212> TYPE: PRT
<213> ORGANISM: Homo sapiens

<400> SEQUENCE: 1

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150
```

SYNTHETIC RETINA

RELATED APPLICATIONS

This application is a national stage filing under 35 U.S.C. § 371 of international application PCT/GB2015/050441, filed Feb. 16, 2015, which claims priority to UK Application No. 1402692.6, filed Feb. 16, 2014. Each of the prior applications is incorporated by reference in its entirety.

This invention relates to a culture method for producing a synthetic retina. Uses of the retina are also provided. The invention also provides defined media for use in the methods.

BACKGROUND

Blindness represents an increasing global problem with social and economic impacts both for the patients and society in general. In Europe, approximately 1 in 30 individuals experience sight loss and 75% of those are unemployed, a social burden which is very likely to increase as the population of Europe ages.

Diseases affecting the retina, the light sensitive extension of the central nervous system lining the back of the eye, account for approximately 26% of blindness. To date, there are no treatments to restore lost retinal cells and visual function and there is an urgent need for new therapeutic approaches. A pioneering breakthrough has highlighted the possibility of generating synthetic retinae from stem cells under laboratory conditions, a finding with immense relevance for basic research, in vitro disease modelling, drug discovery and cell replacement therapies. This research however is in its infancy and needs to be developed so human synthetic retinae can be produced at high efficiency and reproducibly from patient-specific pluripotent stem cells.

Diseases affecting the outer retina including age related macular degeneration (AMD) and inherited retinal dystrophies (HRDs) account for approximately 26% of blindness and the number affected is expected to double by the 2020 due to ageing of the world's population. Although in some cases, the initial trigger event is the degeneration of retinal pigmented epithelium (RPE, a monolayer of pigmented cells forming part of the blood/retina barrier), the final impact in both AMD and HRDs is the loss of photoreceptors, a specialised type of photosensitive neurons that are capable of photo-transduction. Whilst there are a number of agents (including high dose antioxidants, neuronal survival agents, vascular endothelial growth factor inhibitors etc) that have been shown to slow disease progression, to date there are no treatments to restore lost photoreceptors and visual function, hence there is a pressing need for research into the replacement and/or reactivation of dysfunctional photoreceptors and RPE.

A key reason for using stem cell based therapies to treat retinal disorders is the prospect of generating unlimited quantities of desired cell types for transplantation. In this regard a variety of stem cell types have been investigated and pluripotent stem cells have emerged as the best source for several reasons. Firstly, the only cell type shown to integrate and show function within host retina to-date are murine postmitotic photoreceptor precursors isolated at a very specific time of embryonic development. However, if this was to be translated into a human scenario, then the equivalent human cells would need to be isolated from the second trimester of a human foetus, which raises many ethical concerns. Moreover, it has recently been shown that murine embryonic stem cells (ESC) are able to generate self-organising optic cups when cultured under three dimensional (3D) minimal culture conditions. Most importantly, these murine ESC derived optic cups undergo differentiation to give rise to a fully laminated neural retina containing all the main retinal cell types including the light sensitive photoreceptors, following the normal sequence of retinal development (FIG. 10). These findings highlight an important facet of ESC biology that is essential for the field of retinal regeneration: a latent intrinsic ability to give rise to self-organised neural retina which can be exploited to produce synthetic retinae in vitro.

Cell replacement therapy remains an important goal for patients suffering from blinding forms of outer retinal degeneration characterized by a substantial loss of light-sensitive photoreceptors and the underlying retinal pigmented epithelium (RPE). Progress towards the clinic is being made with regards to RPE production and replacement from human pluripotent cells, (Schwartz, S. D., Hubschman, J. P., Heilwell, G., Franco-Cardenas, V., Pan, C. K. et al. Embryonic stem cell trials for macular degeneration: a preliminary report. *The Lancet* 379 (9817), 713-20 (2012); 2. ACT Clinical Trial: Safety and Tolerability of Sub-retinal Transplantation of hESC Derived RPE (MA09-hRPE) Cells in Patients With Advanced Dry Age Related Macular Degeneration (Dry AMD). http://clinicaltrials.gov/ct2/show/NCT01344993 (2011a); 3. ACT Clinical Trial: Sub-retinal Transplantation of hESC Derived RPE (MA09-hRPE) Cells in Patients With Stargardt's Macular Dystrophy. http://clinicaltrials.gov/ct2/show/NCT01345006 (2011 b); 4. ACT Clinical Trial: Safety and Tolerability of Sub-retinal Transplantation of Human Embryonic Stem Cell Derived Retinal Pigmented Epithelial (hESC-RPE) Cells in Patients With Stargardt's Macular Dystrophy (SMD). http://clinicaltrials-.gov/ct2/show/NCT01469832 (2011c) yet, achieving the same momentum for photoreceptor replacement has been more difficult.

Recent studies have demonstrated that there are species specific differences in the ability to produce stratified retina in vitro (Nakano et al. (2012) Cell Stem Cell. 10:771-85). Optic cup formation in mice (using ESC's) takes approximately 28 days, whereas the same optic cup formation process takes approximately 126 days in humans. The human ESC (hESC) derived optic cups are slower to develop, rarely contain RPE, predominantly generate cones and the culture system requires inclusion of fetal bovine serum which can show batch to batch variability and hence is not suitable for clinical applications.

It has previously been shown that it is possible to drive the differentiation of hESC and human induced pluripotent stem cells (hiPSC) towards a retinal photoreceptor lineage, generating cells which share a similar gene expression profile, antigen expression and can elicit a similar electrophysiological profile to native photoreceptors (Lamba, D. A., Karl, M. O., Ware, C. B., Reh, T. A. Efficient generation of retinal progenitor cells from human embryonic stem cells. *Proc Natl Acad Sci USA* 103(34), 12769-74 (2006); Osakada, F., Ikeda, H., Mandai, M., Wataya, T., Watanabe, K. et al. Toward the generation of rod and cone photoreceptors from mouse, monkey and human embryonic stem cells. *Nat Biotechnol* 26(2), 215-24 (2008); Osakada, F., Jin, Z. B., Hirami, Y., Ikeda, H., Danjyo, T. et al. In vitro differentiation of retinal cells from human pluripotent stem cells by small-molecule induction. *J Cell Sci.* 122(17), 3169-79 (2009); Hirami, Y., Osakada, F., Takahashi, K., Okita, K., Yamanaka, S. et al. Generation of retinal cells from mouse and human induced pluripotent stem cells. *Neurosci Lett* 458(3), 126-31

(2009); Meyer, J. S., Shearer, R. L., Capowski, E. E., Wright, L. S., Wallace, K. A., Modeling early retinal development with human embryonic and induced pluripotent stem cells. *Proc Natl Acad Sci USA* 106(39), 16698-703 (2009); Meyer, J. S., Howden, S. E., Wallace, K. A., Verhoeven, A. D., Wright, L. S. et al. Optic vesicle-like structures derived from human pluripotent stem cells facilitate a customized approach to retinal disease treatment. *Stem Cells.* 29(8), 1206-18 (2011); Jin, Z. B., Okamoto, S., Osakada, F., Homma, K., Assawachananont, J. et al. Modeling retinal degeneration using patient-specific induced pluripotent stem cells. *PLoS One* 6(2), e17084 (2011); Amirpour, N., Karamali, F., Rabiee, F., Rezaei, L., Esfandiari, E. et al. Differentiation of human embryonic stem cell-derived retinal progenitors into retinal cells by Sonic hedgehog and/or retinal pigmented epithelium and transplantation into the subretinal space of sodium iodate-injected rabbits. *Stem Cells Dev.* 21(1), 42-53 (2012); Phillips, M. J., Wallace, K. A., Dickerson, S. J., Miller, M. J., Verhoeven, A. et al. Bloodderived Human iPS Cells Generate Optic Vesicle-like Structures with the Capacity to Form Retinal Laminae and Develop Synapses. *Invest Ophthalmol Vis Sci.* 53(4), 2007-19 (2012); Mellough, C. B., Sernagor, E., Moreno-Gimeno, I., Steel, D. H., Lako, M. Efficient stagespecific differentiation of human pluripotent stem cells toward retinal photoreceptor cells. *Stem Cells.* 30(4), 673-86 (2012); Nakano, T., Ando, S., Takata, N., Kawada, M., Muguruma, K. et al. Self-Formation of Optic Cups and Storable Stratified Neural Retina from Human ESCs. *Cell Stem Cell.* 10(6), 771-85 (2012)). To date no human studies have shown reproducible methods that produce outer segment formation, that is necessary for phototransduction (Banin, E., Obolensky, A., Idelson, M., Hemo, I., Reinhardtz, E. et al. Retinal incorporation and differentiation of neural precursors derived from human embryonic stem cells. *Stem Cells.* 24(2), 246-57 (2006); Lamba, D. A., Gust, J., Reh, T. A. Transplantation of human embryonic stem cell-derived photoreceptors restores some visual function in Crx-deficient mice. *Cell Stem Cell.* 4(1), 73-9 (2009); Lamba, D. A., McUsic, A., Hirata, R. K., Wang, P. R., Russell, D. et al. Generation, purification and transplantation of photoreceptors derived from human induced pluripotent stem cells. *PLoS ONE.* 5(1), e8763 (2010)). While early postmitotic primary mouse photoreceptors can successfully integrate and develop outer segments following subretinal transplantation into the mouse eye, (MacLaren, R. E., Pearson, R. A., MacNeil, A., Douglas, R. H., Salt, T. E. et al. Retinal repair by transplantation of photoreceptor precursors. *Nature.* 444(7116), 203-7 (2006); Lakowski, J., Baron, M., Bainbridge, J., Barber, A. C., Pearson, R. A. et al. Cone and rod photoreceptor transplantation in models of the childhood retinopathy Leber congenital amaurosis using flow-sorted Crx-positive donor cells. *Hum Mol Genet.* 19(23), 4545-59 (2010)) in human studies the absence of the outer segment both in vitro and post-transplantation in vivo renders this approach ineffective for disease modelling and visual restoration.

Mellough, C. B., et al (2012) describes differentiation of human pluripotent stem cells toward retinal photoreceptor cells with the final stage of photoreceptor maturation occurring under two dimensional (2D) culture conditions. This published protocol uses supplements and growth factors shown to be important for eye field and retinal development and results in efficient generation of cone and rod photoreceptors (up to 85%) within 45 days. To test the functionality of the hESC derived photoreceptors, the inventors carried out sub-retinal transplantations in normal adult mice and mouse models of retinal degeneration (Pde6b$^{rd1}$ and Crx$^{-/-}$); however the results show that although these cells engraft within the appropriate retinal layer (outer nuclear layer), the engraftment efficiency was low (less than 4%). Upon transplantation, hESC derived photoreceptors failed to develop photoreceptor outer segments (an essential component of a photoreceptor cell type for the phototransduction process) and only in very rare cases did the engrafted cells acquire the expression of photoreceptor markers. These findings suggest that differentiation of hESC/hiPSC under 2D culture conditions may not be the ideal route for generating fully mature and functional photoreceptors.

Accordingly, there remains a need for a method that is capable of producing sufficient numbers of photoreceptor precursors of the correct developmental stage to repair adult retina from hESC/hiPSC.

BRIEF SUMMARY OF THE DISCLOSURE

In accordance with the present inventions there is provided a method of producing a synthetic retina, comprising:
i) providing a three dimensional stem cell culture,
ii) differentiating the three dimensional stem cell culture for a first time period in a first neural cell culture medium comprising:
a) L-glutamine;
b) B27 supplement; and
c) an IGF-1 receptor agonist,
iii) subsequently differentiating the three dimensional stem cell culture for a second time period in a second neural cell culture medium comprising:
a) L-glutamine;
b) B27 supplement;
c) N2 supplement; and
d) an IGF-1 receptor agonist,
wherein said synthetic retina contains laminated retinal tissue comprising photoreceptors.

In one embodiment, the retinal tissue comprises one or more, preferably at least two, of the following cell types: bipolar cells, amacrine cells, ganglion cells and retinal pigmented epithelium (RPE) cells. In one embodiment the retinal tissue comprises an outer layer containing photoreceptors and/or an inner nuclear layer and/or a retinal ganglion cell layer.

In one embodiment said first neural cell culture medium further comprises Dulbecco's Modified Eagle Medium (DMEM), Nutrient Mixture F-12 (F-12), or a combination thereof.

In one embodiment said second neural cell culture medium further comprises Dulbecco's Modified Eagle Medium (DMEM), Nutrient Mixture F-12 (F-12), or a combination thereof.

In one embodiment said first neural cell culture medium and/or wherein said second neural cell culture medium further comprises Non-essential amino acid (NAA).

In one embodiment said first neural cell culture medium further comprises Knockout serum replacement (KOSR), preferably wherein the amount of Knockout serum replacement (KORS) in the first neural cell culture medium is reduced during the first time period.

In a further aspect there is provided a method of producing a synthetic retina, comprising:
i) providing a three dimensional stem cell culture;
ii) differentiating the three dimensional stem cell culture for a first time period in a first neural cell culture medium comprising an IGF-1 receptor agonist;
iii) subsequently differentiating the three dimensional stem cell culture for a second time period in a second neural cell culture medium comprising an IGF-1 receptor agonist, wherein said synthetic retina contains laminated retinal tissue comprising photoreceptors and wherein said first and second neural cell culture medium do not comprise each of recombinant mouse Noggin (rmNoggin), recombinant human Dickkopf-1 (Dkk1), recombinant human Lefty A (rh Lefty A), Human Sonic Hedgehog (Shh), 3,3',5-triiodo-L-thyronine (T3), recombinant human Basic Fibroblast Growth Factor (rhbFGF), retinoic acid, taurine and Human Activin-A.

In one embodiment said first neural cell culture medium further comprises B27 supplement.

In one embodiment said first neural cell culture medium further comprises L-glutamine.

In one embodiment said first neural cell culture medium further comprises Knockout serum replacement (KOSR), preferably wherein the amount of Knockout serum replacement (KORS) in the first neural culture cell medium is reduced during the first time period.

In one embodiment said second neural cell culture medium further comprises B27 supplement.

In one embodiment said second neural cell culture medium further comprises L-glutamine.

In one embodiment said second neural cell culture medium further comprises N-2 supplement.

In one embodiment said stem cell culture consists of human induced pluripotent stem cells (hiPSC).

In one embodiment said three dimensional stem cell culture is an embryoid body (EB) culture.

In one embodiment said first time period is from about 30 to about 40 days. Preferably, said first time period is about 37 days.

In one embodiment said second time period is from about 30 to 90 days, alternatively about 30 to about 60 days. Preferably, said second time period is about 53 days.

In one embodiment of any of the aforementioned methods said IGF-1 receptor agonist is selected from the group consisting of:
  i) a human IGF-1;
  ii) a homologue of human IGF-1; or
  iii) an analogue of human IGF-1.

Preferably, said human IGF-1 is a recombinant human IGF-1, preferably a recombinant human IGF-1 having the polypeptide sequence of SEQ ID NO:1.

Preferably, said homologue of human IGF-1 has at least 80% identity to the recombinant human IGF-1 having the polypeptide sequence of SEQ ID NO:1.

In one embodiment of any of the aforementioned methods said method further comprising a step of isolating said synthetic retina from said second neural cell culture medium.

In a further aspect there is provided a synthetic retina obtainable by the method of any one of the aforementioned methods.

In a further aspect there is provided a pharmaceutical composition comprising the aforementioned synthetic retina.

In a further aspect there is provided the aforementioned synthetic retina or pharmaceutical composition for use in the treatment of retinal disease or ocular injury.

In one embodiment the retinal disease is a retinal degenerative disease. Preferably, the retinal degenerative disease is selected from the group consisting of Retinitis Pigmentosa, age-related macular degeneration, Bardet-Biedel syndrome, Bassen-Kornzweig syndrome, Best disease, choroideremia, gyrate atrophy, Leber congenital amaurosis, Refsun syndrome, Stargardt disease or Usher syndrome.

In a further aspect there is provided the aforementioned synthetic retina for use as a tissue graft.

In one embodiment the stem cell culture consists of human induced pluripotent stem cells (hiPSC) obtained from a subject to be treated.

In a further aspect there is provided use of the aforementioned synthetic retina in an in vitro model for retinal or neurological disease.

In a further aspect there is provided use of the aforementioned synthetic retina in a screen to identify compounds useful in the treatment of retinal or neurological disease.

In a further aspect there is provided a defined media comprising:
  a)
  L-glutamine;
  b) B27 supplement; and
  c) an IGF-1 receptor agonist.

In a further aspect there is provided a defined media comprising:
  a) L-glutamine;
  b) B27 supplement;
  c) N2 supplement; and
  d) an IGF-1 receptor agonist.

BRIEF DESCRIPTION OF THE DRAWINGS

Embodiments of the invention are further described hereinafter with reference to the accompanying drawings, in which:

FIG. 12 shows the amino acid sequence of human IGF-1 (as shown at http://www.ncbi.nlm.nih.gov/qene/3479# reference-sequences IGF-1 RefSeqGene: http://www.ncbi.nim.nih.gov/nuccore/ NG_01173.1?from=5001&to=89734&report=genban k).

DETAILED DESCRIPTION

Figure 1:
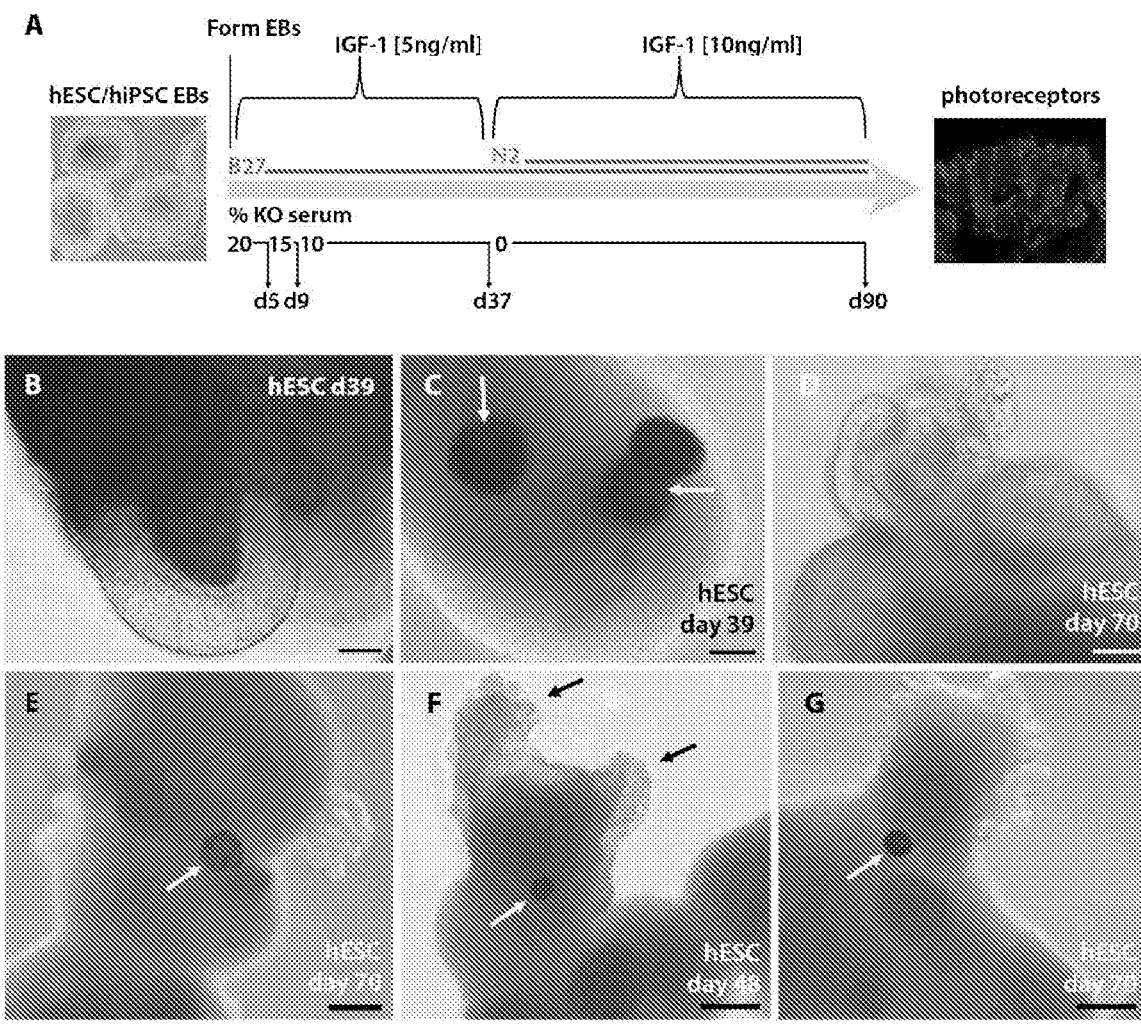
FIG. 1 provides a schematic of the inventor's differentiation protocol and examples of the gross morphology of floating hESC-derived EBs which displayed developmental features associated with neural and retinal development. (A) For differentiation hESC/hiPSCs were grown as EBs in reducing concentrations of knockout (KO) Serum, then as serum-free cultures from day 37 until day 90. Cultures were treated with 5 ng/ml IGF-1 over days 0-37 and thereafter with 10 ng/ml IGF-1. B27 was used as a supplement throughout differentiation, with the addition of N2 supplement from day 37 onwards. (B-G) Phase micrographs showing structures developing from EBs under control culture conditions (no IGF-1, B, D), PR-induction conditions with all factors (C) or IGF-1 treatment (E-G). Pictures (F) and (G) show the same EB at day 48 then 70, demonstrating how bilateral neuroepithelial folds emanating from EBs (E, arrows) fold and become more convoluted with time. Scale bars; B=50 μm, C,D=100 μm, E-G=200 μm.

Under basal media conditions, hESC and hiPSC are capable of exhibiting neural, eye field, retinal and photoreceptor gene expression over time and can produce various retinal phenotypes in the absence of inductive cues, suggestive of an intrinsic ability that can be exploited to optimise the differentiation process. (Meyer, J. S., Howden, S. E., Wallace, K. A., Verhoeven, A. D., Wright, L. S. et al. Optic vesicle-like structures derived from human pluripotent stem cells facilitate a customized approach to retinal disease treatment. Stem Cells. 29(8), 1206-18 (2011); Mellough, C. B., Sernagor, E., Moreno-Gimeno, I., Steel, D. H., Lako, M. Efficient stagespecific differentiation of human pluripotent stem cells toward retinal photoreceptor cells. Stem Cells. 30(4), 673-86 (2012)). The inventors have now surprisingly shown that the addition of culture supplements and growth factors can accelerate or enhance this default pathway (Mellough, C. B., Sernagor, E., Moreno-Gimeno, I., Steel, D. H., Lako, M. Efficient stagespecific differentiation of human pluripotent stem cells toward retinal photoreceptor cells. Stem Cells. 30(4), 673-86 (2012)). In a screen of mitogens and growth factors, an important role for the neural supplement B27 during the early stages of hESC/hiPSC differentiation was identified.

The inventors have now surprisingly identified that the addition of a single factor, insulin-like growth factor 1 (IGF-1), to hESC/hiPSC cultures for the entire period of differentiation can orchestrate the generation of ocular-like structures containing various elements of the developing eye including RPE, neural retina, primitive lens and cornea. Furthermore the retinal tissue observed is advantageously organised with a laminar pattern reminiscent of the developing human retina. The hESC/hiPSC-derived retinal tissue comprises multiple phenotypes, including photoreceptors, bipolar, amacrine and ganglion cells, which form synaptic connections and allow the formation of a visible plexiform layer. The inventors have also observed the development of rod- and cone-like photoreceptor inner and outer segments from these hESC/hiPSC-derived photoreceptor cells and have demonstrated that these cells are capable of producing phototransduction related electrical responses, making these derivatives excellent candidates for cell replacement studies in addition to in vitro disease modelling.

Moreover, the methods of the invention can be used to generate synthetic retinae under good manufacturing practice (GMP) conditions from hESC and hiPSC.

The inventors have identified for the first time the role of IGF-1 in human retinal ontogenesis.

Cells and Culture Conditions

In a first aspect the invention provides a method of producing a synthetic retina, comprising: i) providing a three dimensional stem cell culture, ii) differentiating the stem cell culture for a first time period in a first neural cell culture medium comprising: a) L-glutamine; b) B27 supplement; and c) an IGF-1 receptor agonist, iii) subsequently differentiating the stem cell culture for a second time period in a second neural cell culture medium comprising: a) L-glutamine; b) B27 supplement; c) N2 supplement; and d) an IGF-1 receptor agonist, wherein said synthetic retina contains laminated retinal tissue comprising photoreceptors.

In a further aspect the invention provides a method of producing a synthetic retina, comprising: i) providing a three dimensional stem cell culture; ii) differentiating the stem cell culture for a first time period in a first neural cell culture medium comprising an IGF-1 receptor agonist; iii) subsequently differentiating the stem cell culture for a second time period in a second neural cell culture medium comprising an IGF-1 receptor agonist, wherein said synthetic retina contains laminated retinal tissue comprising photoreceptors and wherein said first and second neural cell culture medium do not comprise each of recombinant mouse Noggin (rmNoggin), recombinant human Dickkopf-1 (Dkk1), recombinant human Lefty A (rh Lefty A), Human Sonic Hedgehog (Shh), 3,3',5-triiodo-L-thyronine (T3), recombinant human Basic Fibroblast Growth Factor (rhbFGF), retinoic acid, taurine and Human Activin-A.

As used herein the phrase "do not comprise" relates to the culture media not being supplemented with or being essentially free from the stated component.

As used herein, the terms "culture" and "cell culture" are used interchangeably refer to the process whereby cells, preferably stem cells, are grown under controlled conditions, preferably in vitro.

As used here in the term "stem cells" refers to pluripotent cells characterised by indefinite self-renewal ability and the capacity to give rise to any cell type in the adult. The term includes human embryonic stem cells (hESC) and human induced pluripotent stem cells (hiPSCs). hESC are derived from spare in vitro fertilised embryos after parental consent and have been widely used in the last decade as a generic tool to understand maintenance of pluripotency, human embryonic development and congenital disease. Destruction of human embryos for research purposes is surrounded by a number of ethical issues, prohibiting hESC derivation and application in several countries. However the main issue related to their application is the evidence that their differentiated progeny express human leukocyte antigens (HLAs) that will probably result in graft rejection and could be bypassed only by creation of HLA-typed hESC banks, from which a best match can be selected. Human iPSC bypass both of these issues as they are generated by reprogramming somatic cells back to the pluripotent state akin to embryonic stem cells. As such, these cells share all the characteristics of hESC including the ability to proliferate indefinitely and differentiate into many cell types, but also represent a source of autologous stem cells for cell replacement therapies given that they are derived from the patient themselves. Such patient derived cells present a unique opportunity to create in vitro disease models which can be exploited to understand disease pathology and drug discovery. This becomes extremely important for degenerative diseases such as those affecting the retina, where availability of patient specific cells (i.e. photoreceptors and RPE) becomes a possibility only after invasive surgery or death. New tools developed in the gene therapy field including improved and safer viral vectors as well as the possibility of correcting endogenous mutations through the application of site specific restriction endonucleases (such as Zinc Finger Nucleases, known as ZFN or Transcription Activator-Like Effector Nucleases also known as TALEN), also mean that functional patient specific cells for transplantation can be produced from hiPSC.

As used herein the term "medium" and "media" are used interchangeably.

As used herein "neural cell culture medium" is used to refer to a culture media containing the minimum essential elements necessary to maintain the growth of a neural cell. Such neural cell culture media typically comprise roughly fifty chemical entities at known concentrations in water. The chemical components of the culture media fall into five broad categories: amino acids, vitamins, inorganic salts, trace elements, and a miscellaneous category that defies neat categorization. In addition, neural cell culture medium preferably comprises glucose, most preferably D-glucose.

Defined culture media comprising minimum essential elements necessary to maintain the growth of neural cells are well known in the art and include, by way of example only Minimum Essential Medium Dulbecco, F12 (HAM), RPMI 1640, advanced RPMI, Dulbecco's Modified Eagle Medium (DMEM—without serum), Knockout DMEM, Knockout DMEM:F12, DMEM (high glucose), Neurobasal, Neurobasal A, Glasgow Modification Eagle Medium (GMEM), Leibovitz L-15 Medium, McCoy's 5A Medium and Waymouth's medium.

In one embodiment of each of the aforementioned aspects, the first neural cell culture medium comprises: a) L-glutamine; b) B27 supplement; and c) an IGF-1 receptor agonist.

In one embodiment of each of the aforementioned aspects, the second neural cell culture medium comprises: a) L-glutamine; b) B27 supplement; c) N2 supplement; and d) an IGF-1 receptor agonist.

As used herein "B27 supplement" refers to a neural cell culture supplement, such as B-27® serum-free supplement (Life Technologies). Preferably, the supplement comprises Probably T3, insulin and vitamin A.

As used herein "N-2 supplement" refers to a supplement for the growth and expression of post-mitotic neurons and tumor cells of neuronal phenotype, for example a Bottenstein's N-1 or N-2 supplement, most preferably Bottenstein's N-2 supplement (Life Technologies). Preferably, the supplement comprises Human Transferrin and Insulin, more preferably the supplement comprises Human Transferrin, Insulin, Progesterone, Putrescine and Selenite.

In one embodiment of each of the aforementioned aspects, a preferred medium for use in the first neural cell culture medium of the present invention comprises the commercially available media DMEM-Hams F-12 (Life Technologies).

In one embodiment of each of the aforementioned aspects, a preferred medium for use in the second neural cell culture medium of the present invention comprises the commercially available media DMEM-Hams F-12 (Life Technologies).

In each of the aforementioned aspects, both of the first neural cell culture medium and second neural cell culture medium are supplemented with an (insulin-like growth factor) IGF-1 receptor agonist. As used herein, the term "IGF-1 receptor agonist" refers to any compound, for example a peptide, which is capable of acting at insulin-like growth factor receptor as an agonist, i.e. acts as a ligand that elicits insulin-like growth factor receptor activity. Preferably the agonist is Insulin-like growth factor 1 (IGF-1). More preferably, the IGF-1 is human IGF-1, or a homologue or analogue thereof.

IGF-I is a single-chain, 70-amino-acid protein with high homology to proinsulin, the sequence of which is shown in FIG. 12 (UniProtKB P00750, P05019-2, Isoform 2, also known as IGF-1A). Unlike the other members of the insulin superfamily, the C region of –IGF's is not proteolytically removed after translation. The solution NMR structures of IGF-I (Cooke et al., Biochemistry, 30: 5484-5491 (1991); Hua et al., J. Mol. Biol., 259: 297-313 (1996)), mini-IGF-I (an engineered variant lacking the C-chain; DeWolf et al., Protein Science, 5: 2193-2202 (1996)), and IGF-II (Terasawa et al., EMBO J. 13: 5590-5597 (1994); Torres et al., J. Mol. Biol. 248: 385-401 (1995)) have been reported. It is generally accepted that distinct epitopes on IGF-I are used to bind receptor and binding proteins. It has been demonstrated in animal models that receptor-inactive IGF mutants are able to displace endogenous IGF-I from binding proteins and thereby generate a net IGF-I effect in vivo (Loddick et al., Proc. Natl. Acad. Sci. USA, 95: 1894-1898 (1998); Lowman et al., Biochemistry, 37: 8870-8878 (1998); U.S. Pat. Nos. 6,121,416 and 6,251,865).

Preferably the IGF-1 is at least 60%, 65%, 70%, 75%, 80%, 85%, 90%, 91%, 92%, 93%, 94%, 95%, 96%, 97%, 98%, 99% or 100% identity to the entire length of the polypeptide sequence shown in SEQ ID NO:1.

As used herein, the terms "homology" and "identity" are used interchangeably. Calculations of sequence homology or identity between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

Alternatively, the percent identity between two amino acid or nucleotide sequences can be determined using the algorithm of Meyers et al. (1989) *CABIOS* 4:11-17) which has been incorporated into the ALIGN program (version 2.0), using a PAM120 weight residue table, a gap length penalty of 12 and a gap penalty of 4.

Many mutagenesis studies have addressed the characterization of the IGFBP-binding epitope on IGF-I (Bagley et al., Biochem. J., 259: 665-671 (1989); Baxter et al., J. Biol. Chem., 267: 60-65 (1992); Bayne et al., J. Biol. Chem., 263: 6233-6239 (1988); Clemmons et al., J. Biol. Chem., 265: 12210-12216 (1990); Clemmons et al., Endocrinology, 131: 890-895 (1992); Oh et al., supra.

Variants of IGF-1 have been disclosed. WO 96/33216 describes a truncated variant having residues 1-69 of authentic IGF-I. EP742228 discloses two-chain IGF-I superagonists that are derivatives of the naturally occurring single-chain IGF-I having an abbreviated C domain. Cascieri et al., Biochemistry, 27: 3229-3233 (1988) discloses mutants of IGF-I,] Cascieri et al., J. Biol. Chem., 264: 2199-2202 (1989) discloses three IGF-I analogs in Sliecker et al., Adv. Experimental Med. Biol., 343: 25-32 (1994)) describes the binding affinity of various IGF and insulin variants to IGFBPs, IGF receptor, and insulin receptor. The IGF-1 agonist may be an IGF-1 variant.

In one embodiment of each of the aforementioned aspects, both of the first neural cell culture medium and second neural cell culture medium are serum free culture media, i.e. a medium that contains no serum (e.g., fetal bovine serum (FBS), horse serum, goat serum, etc.).

In one embodiment of each of the aforementioned aspects, said second neural cell culture medium is supplemented with a serum-free eukaryotic cell culture medium supplement, for example KnockOut™ Serum Replacement media supplement, Essential 6 Medium (both Life Technologies), and TeSR-E6 (Stem Cell Technologies).

In one embodiment of each of the aforementioned aspects, the first neural cell culture medium and/or the second neural cell culture medium is supplemented with an amino acid, such as a Non-Essential Amino Acid media supplement (NEAA, Life Technologies).

In one embodiment of each of the aforementioned aspects, the first neural cell culture medium and/or the second neural cell culture medium may be further supplemented with antibiotics, albumin, amino acids, or other components known in the art for the culture of cells.

In one preferred embodiment of each of the aforementioned aspects, the first neural cell culture medium consists of: a) Dulbecco's Modified Eagle Medium (DMEM), Nutrient Mixture F-12 (F-12), or a combination thereof; b) knockout serum replacement (KOSR); c) L-glutamine; d) Non essential amino acid (NEAA); e) B27 supplement; and f) an IGF-1 receptor agonist.

In one preferred embodiment of each of the aforementioned aspects, the first neural cell culture medium consists of: a) Dulbecco's modified Eagle Medium (DMEM), Nutrient Mixture F-12 (F-12), or a combination thereof; b) L-glutamine; c) Non essential amino acid (NEAA); d) B27 supplement; e) N2 supplement; and f) an IGF-1 receptor agonist.

In one preferred embodiment of each of the aforementioned aspects the first neural cell culture medium consists of: a) Dulbecco's Modified Eagle Medium (DMEM), Nutrient Mixture F-12 (F-12), or a combination thereof; b) knockout serum replacement (KOSR); c) L-glutamine; d) Non essential amino acid (NEAA); e) B27 supplement; and f) an IGF-1 receptor agonist and the first neural cell culture medium consists of: a) Dulbecco's modified Eagle Medium (DMEM), Nutrient Mixture F-12 (F-12), or a combination thereof; b) L-glutamine; c) Non essential amino acid (NEAA); d) B27 supplement; e) N2 supplement; and f) an IGF-1 receptor agonist.

As used herein "three dimensional stem cell culture" refers to a cell culture having three-dimensional (3D) culture structure and is distinct from cultures grown on 2D substrates. Preferably, said three dimensional stem cell culture is embryoid body (EB) culture. The term "embryoid body" or "EB" refers to collections of cells formed from the aggregation or clustering of cultured embryonic stem cells in culture. EBs have a three-dimensional morphology, e. g., they can be a solid or a cystic embryoid body. Alternatively, the 3D stem cell culture may be grown within a bioreactor or spinner flask, as hanging drops from the lid of tissue culture vessels or within a scaffold or matrix, such as matrigel. Examples of such cultures are known in the art, such as Lancaster et al, Nature. 2013 Sep. 19; 501(7467): 373-9. doi: 10.1038/nature12517. Epub 2013 Aug. 28.

As used herein said first time period may be from about 20 to 40 days, preferably about 30 to 40 days, preferably about 33 to 38 days, most preferably about 37 days.

As used herein said second time period may be from about 30 to about 90 days, preferably about 30 to about 60 days, preferably about 40 to 57 days, most preferably about 53 days.

In one preferred embodiment of each of the aforementioned aspects, said first time period is about 37 days and the second time period is about 53 days.

In one embodiment the step of differentiating the three dimensional stem cell culture is feeder free.

Prior to differentiation, the three dimensional stem cell culture may be expanded either under feeder or feeder free conditions.

Preferably the step of differentiating the three dimensional stem cell culture is feeder free.

Synthetic Retina

Emergence of the early synthetic retina is characterised by phase bright neuroepithelium (expressing Rax/Pax6) which evaginates from the edge of differentiating EB's, akin to the optic vesicles during normal development. This develops over time to form a bilayered optic cup. The inner wall of the cup contains retinal progenitors (expressing Pax6, Chx10) which subsequently differentiate into more mature retinal phenotypes and migrate to finally reside within distinct retinal neural layers, forming fully laminated retina (with different retinal phenotypes expressing Crx, Recoverin, Opsin, Calbindin 28, TUJ1, HuC/D and Islet1/2). The outer wall of the cup gives rise to retinal pigmented epithelium, characterised by its dark pigmentation and expression of RPE65 and ZO-1, which arises in parallel alongside neural retinal tissue.

Medical Uses

The synthetic retinae of the invention are of particular use in various therapeutic settings. In particular, the synthetic retinae are of particular use in transplantation and engraftment, for example to treat disease, injury or wounding.

Accordingly, the invention provides the use of the synthetic retinae of the invention as a medicament.

The invention also provides a method of treating an ocular disease or injury comprising implanting a synthetic retina of the invention into the eye of a mammalian subject in need thereof.

Generally the ocular disease or injury is related to a damaged retina and/or retinal degenerative.

As used herein, the term "ocular injury" refers to conditions resulting in an insufficient stromal micro-environment to support stem cell function, for example aniridia, keratitis, neurotrophic keratopathy, Keratoconus, Meesman's dystrophy, Epithelial Basement Membrane Dystrophy and chronic limbitis; or conditions that destroy limbal stem cells such as Partial limbal stem cell deficiency, Total stem cell deficiency, Ocular herpes, chemical or thermal injuries, Stevens-Johnson syndrome, ocular cicatricial pemphigoid, contact lens wear, or microbial infection.

As used herein the term "retinal degenerative disease" refers to a disease or disorder selected from Retinitis Pigmentosa, age-related macular degeneration, Bardet-Biedel syndrome, Bassen-Kornzweig syndrome, Best disease, choroideremia, gyrate atrophy, Leber congenital amaurosis, Refsun syndrome, Stargardt disease or Usher syndrome.

Preferably, said synthetic retina is derived from autologous cells, i.e. said cells are derived from the individual to be treated. Alternatively the cells may be non-autologous.

Also provided is a method of retinal replacement, comprising implanting synthetic retina of the invention into the eye of a mammalian subject in need thereof. There is also provided synthetic retina of the invention for use in retinal replacement.

As used herein the terms "wound" and "wounding" relate to damaged tissues, preferably damaged retina, where the integrity of the retina or tissue is disrupted as a result of e.g. external force, bad health status, aging, exposure to sunlight, heat or chemical reaction or as a result from damage by internal physiological processes.

The synthetic retinae and/or compositions of the invention may be placed into the interior of an eye using a syringe, a needle, a cannula, a catheter, a pressure applicator, and the like.

Pharmaceutical Compositions

The invention also provides a pharmaceutical composition comprising a synthetic retina in accordance with the invention together with a pharmaceutically acceptable excipient, diluent or carrier.

In one embodiment the composition further comprises one or more of the following: growth factors, lipids, genes, etc., or compounds for altering the acidity/alkalinity (pH) of the wound, or compounds for altering the growth and performance of the transplanted cells and those at the margins of the wound/injury.

The term "pharmaceutically-acceptable carrier" as used herein means one or more compatible solid or liquid fillers, diluents or encapsulating substances that are suitable for administration into a human. When administered, the pharmaceutical compositions of the present invention are administered in pharmaceutically acceptable preparations. Such preparations may routinely contain pharmaceutically acceptable concentrations of salt, buffering agents, preservatives, compatible carriers, cytokines and optionally other therapeutic agents, preferably agents for use in wound healing such as growth factors, peptides, proteolytic inhibitors, extracellular matrix components, steroids and cytokines. The term "carrier" denotes an organic or inorganic ingredient, natural or synthetic, with which the active ingredient is combined to facilitate the application. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. As used herein, a pharmaceutically acceptable carrier includes any conventional carrier, such as those described in Remington's Pharmaceutical Sciences, by E. W. Martin, Mack Publishing Co, Easton, Pa., 15th Edition (1975).

In a further aspect there is provided a pharmaceutical composition in accordance with the invention for use as a medicament, for example, for use in treating ocular injury, retinal degeneration and/or injury.

The compositions or synthetic retinae of the invention are administered/for administration in effective amounts. An "effective amount" is the amount of a composition or synthetic retinae that alone, or together with further doses, produces the desired response. The compositions or synthetic retinae used in the foregoing methods preferably are sterile and contain an effective amount of the active ingredient for producing the desired response in a unit of weight or volume suitable for administration to a patient. The response can, for example, be measured by measuring the physiological effects of the composition or micro-organ cell composites upon the rate of or extent of disease treatment or retinal repair.

The invention provides a method to decrease the degeneration of a retina associated with a retinal degenerative disease or an ocular injury in a subject in need thereof comprising administration of a pharmaceutical composition of the invention to the subject in an amount effective to decrease further degeneration of the retina and/repair the retina.

Models

The synthetic retinae of the invention provide an in vitro model system. For example the synthetic retinae can be used as a model to provide insight into retinal and neurological development and also to provide insight into retinal and neurological disease development. The use of the synthetic retinae as a model for disease is useful for the diagnosis and treatment of retinal diseases and disorders. The aforementioned uses may involve retinal manipulations or disease modeling (for example induced by pharmacological treatment or genetic modifications) so as to develop drugs, or to diagnose, prevent, limit or cure retinal diseases and disorders.

The synthetic retina of the invention also provide a screening method for identification of candidate molecules for the treatment of retinal diseases and disorders. This screening method is usable for example for preclinical testing of drugs to treat retinal diseases and disorders. Screening methods may be applied onto cell-based models of the present invention. Any suitable screening method known by the skilled person may be applied to the models of the invention.

The synthetic retinae of the invention are useful in drug screening, for example, useful for identification of both direct and indirect pharmacologic agent effects. For example, certain candidate bioactive agents may be added to the model and the effect(s) monitored. For example, cell/cell interactions and cell/extracellular component interactions may be monitored as they may be important in understanding mechanisms of disease and drug function.

In one aspect the synthetic retinae of the invention may be used in a method of screening a bioactive agent for the treatment of a retinal or ocular disease or disorder comprising: a) providing a synthetic retina in accordance with the invention; b) exposing said retina to an agent; and c) determining whether the agent has a therapeutic effect on the retina.

For example, the in vitro synthetic retinae described herein may be used for identification and biological testing of bioactive agents and compounds, particularly neuroactive agents and compounds, or materials that may be suitable for treatment of neurological diseases or disorders in general, and in particular for treatment of retinal diseases and disorders. The described screening methods may be used to identify a bioactive agent that may be suitable for treating a subject who has a neurological, particularly, a retinal disease or disorder.

The screening methods may be used to determine if the bioactive agent alters (increases or decreases in a statistically significant manner) viability of a retinal cell. The screening method may also be used to determine whether the bioactive agent is capable of altering neurodegeneration of neuronal cells (impairing, inhibiting, preventing, abrogating, reducing, slowing the progression of, or accelerating in a statistically significant manner).

Preferably, said exposing comprises contacting (combining, mixing, or otherwise permitting interaction of) a candidate agent with the synthetic retinae under conditions and for a time sufficient to permit interaction between the candidate agent and the synthetic retinae, and then comparing the viability or degeneration of retinal cells in the presence of the candidate agent with the viability of retinal cells in the absence of the candidate agent. For example, retinal cells that are not exposed to a candidate agent may be prepared simultaneously, or alternatively, the effect of an agent may be quantified and compared to viability/degeneration of a standard retinal cell culture (i.e., a retinal cell culture system that provides repeatedly consistent, reliable, and precise determinations of retinal cell viability).

Through use of the synthetic retinae model described herein, agents may be selected and tested that are useful for treating diseases and disorders of the retina. More particularly, the presence of photoreceptors with an intact outer segment is relevant in such an assay to identify compounds useful for treating neurodegenerative eye diseases.

The synthetic retinae model of the invention may be used to screen candidate bioactive agents to determine whether the bioactive agent increases viability of retinal cells. A person skilled in the art would readily appreciate and understand that a retinal cell which exhibits increased viability means that the length of time that a retinal cell survives in the synthetic retinae system is increased (increased lifespan) and/or that the retinal cell maintains a biological or biochemical function (normal metabolism and organelle function; lack of apoptosis; etc.) compared with a retinal cell of a synthetic retinae of control cell system (e.g., the cell culture system described herein in the absence of the candidate agent). Increased viability of a retinal cell may be indicated by delayed cell death or a reduced number of dead or dying cells; maintenance of structure and/or morphology; lack of or delayed initiation of apoptosis; delay, inhibition, slowed progression, and/or abrogation of retinal neuronal cell neurodegeneration or delaying or abrogating or preventing the effects of neuronal cell injury. Methods and techniques for determining viability of a retinal cell and thus whether a retinal cell exhibits increased viability are described in greater detail herein and are known to persons skilled in the art.

For example a bioactive agent that inhibits may be screened by contacting (mixing, combining, the agent and the synthetic retina of the invention), for example, a candidate agent from a library of agents as described herein, with the model under conditions and for a time sufficient to permit interaction between a candidate agent and the synthetic retina as described herein.

Experimental Methodology and Results

The inventors have previously demonstrated that retinal cells can be derived from human embryonic stem cells (hESC) and induced pluripotent stem cells (hiPSC) under defined culture conditions. Whilst both cell types can give rise to retinal derivatives in the absence of inductive cues, this requires extended culture periods and gives lower overall yield. The exploitation of this innate differentiation ability and development of clinically compatible culture conditions to reproducibly generate functional neural retina is an important goal for clinical cell based therapies. The inventors now report that insulin-like growth factor 1 (IGF-1) can orchestrate the formation of ocular-like structures containing retinal pigmented epithelium, neural retina, primitive lens and cornea from hESC/hiPSC in vitro. Inhibition of IGF-1 receptor signalling significantly reduces the formation of optic structures, indicating an important role for IGF-1 as an inducer of retinal differentiation in human. IGF-1 treatment enhances the formation of laminated retinal tissue composed of multiple retinal phenotypes which form synapses and a visible inner plexiform layer, reminiscent of the developing human retina. Primitive rod- and cone-like photoreceptor inner and outer segments were observed and electrophysiological analysis revealed similarity to native photoreceptors, making these derivatives promising candidates for cell replacement studies and in vitro disease modelling.

Experimental Methodology and Results—Introduction

Cell replacement therapy remains an important goal for patients suffering from blinding forms of outer retinal degeneration characterized by the substantial loss of light-sensitive photoreceptors and underlying retinal pigmented epithelium (RPE). Progress towards the clinic is being made with regards to RPE production and replacement from human pluripotent cells,[1-4] yet, achieving the same momentum for photoreceptor replacement has been more difficult. The inventors and others have shown that it is possible to drive the differentiation of hESC and hiPSC towards a retinal photoreceptor lineage,[5-15] generating cells which share a similar gene expression profile, antigen expression and can elicit a similar electrophysiological profile to native photoreceptors. Yet while these photoreceptor-like cells exhibit many similarities to their native counterparts, to date no human studies have shown that these cells have the capacity to develop outer segments in vitro or in vivo en masse, necessary for phototransduction.[16-18] While early postmitotic primary mouse and ESC derived photoreceptor precursors can successfully integrate and develop outer segments following subretinal transplantation into the mouse eye,[19, 20] in human studies, although photoreceptor-like cilia and basal bodies have been demonstrated, the absence of the outer segment both in vitro and post-transplantation in vivo may render this approach ineffective for disease modelling and visual restoration.[16-18]

Under basal media conditions, hESC and hiPSC are capable of exhibiting neural, eye field, retinal and photoreceptor gene expression over time and can spontaneously produce various retinal phenotypes in the absence of inductive cues, suggestive of an innate ability that can be exploited to optimise the retinal differentiation process.[10, 14] The inventors have shown that the addition of growth factors and signalling pathway antagonists known to guide retinal histogenesis during normal development can accelerate and enhance this process.[14] In a screen of mitogens and growth factors, the inventors previously identified an important role for the neural supplement B27 during the early stages of hESC and hiPSC differentiation towards retinal phenotypes. The inventors also observed that cultures differentiated with IGF-1, a known enhancer of eye formation and retinal progenitor expression,[5, 21] resulted in the formation of numerous optic vesicle-like structures.[14] This led us to further investigate the conditions which control the formation of optic-vesicular-like structures from hESC and hiPSC in vitro. The inventors have now performed additional experiments which reveal a key role for the IGF-1 signalling pathway in inducing the formation of ocular-like structures containing stratified neural retina alongside other elements of the developing eye from human pluripotent stem cells in vitro.

Experimental Methodology and Results—Results

2D Vs. 3D Differentiation Culture and Development of the Optic Cup

Figure 2:
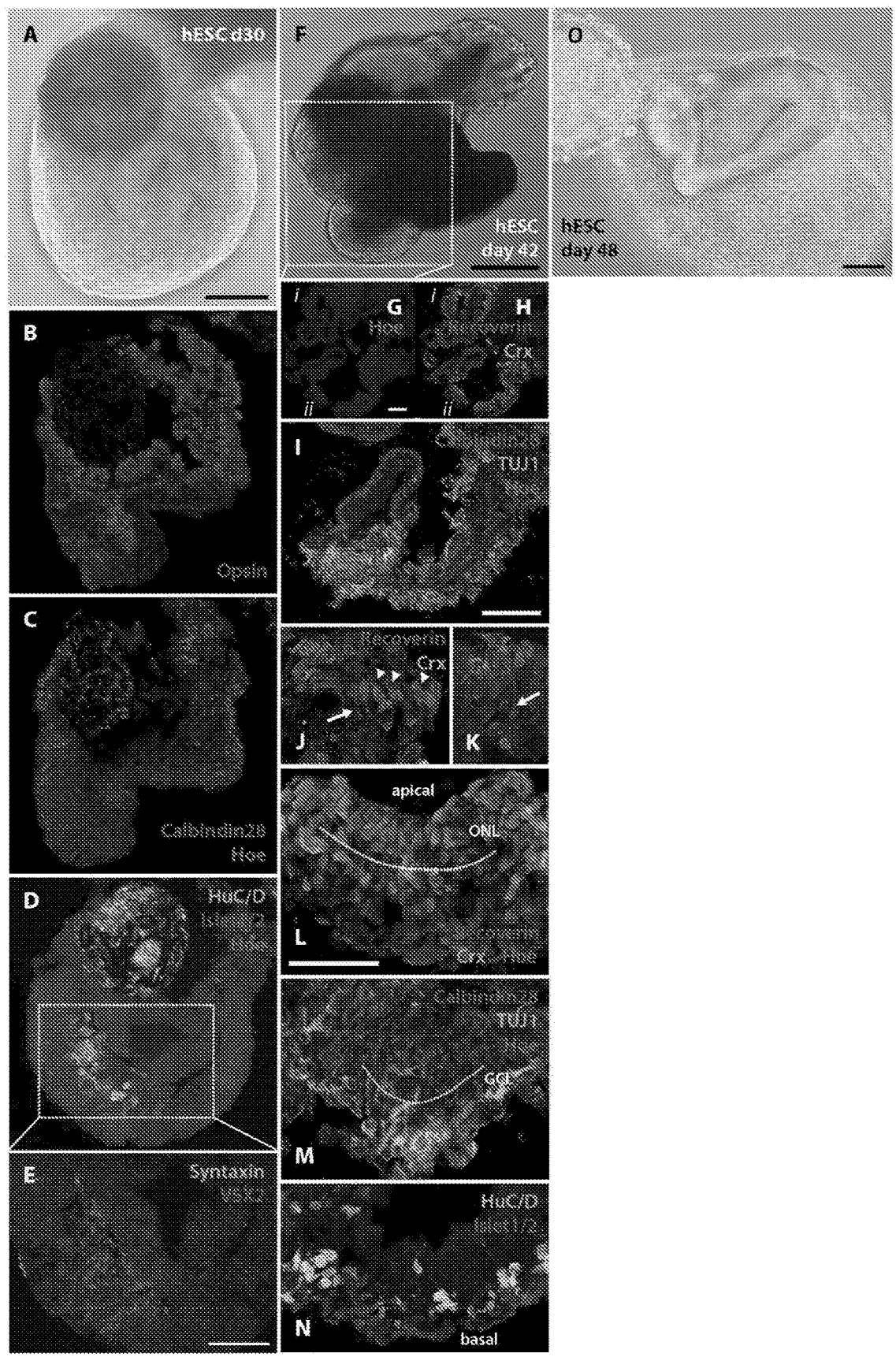
FIG. 2 shows floating EBs differentiating under control conditions can yield primitive optic cup-like structures containing multiple retinal phenotypes. (A-E) The expression of photoreceptor red-green opsin (B), calbindin 28 (C) HuC/D and Islet1/2 (D) indicated the emergence of retinal phenotypes as early as day 30, however mature morphology was not observed at this stage. (E) Enlarged area represented by the dotted line in (D) showing co-localisation of syntaxin staining with HuC/D and Islet1/2 immunopositive cells, indicating the presence of amacrine cells and the formation of an inner plexiform layer. (F-N) An example of clearly identifiable developing retinal tissue arising under control conditions in vitro on day 42 of differentiation (F) which, upon sectioning after 90 days of differentiation (G-N), revealed a region displaying bilateral retinal development (G-I). Retinal tissue contained apically positioned photoreceptors (H, J-L) and basally located ganglion cells (M,N) within the putative outer nuclear (ONL) and ganglion cell (GCL) layers respectively (both depicted by the dotted lines) and medially placed amacrine cells (N). (G-N) Sections through the region demarcated by the dotted line in (F). In some EBs, clear retinal folding could be observed in vitro. Scale bars; A,G,I,O=100 µm, E,L=50 µm, F=200 µm
Figure 8:
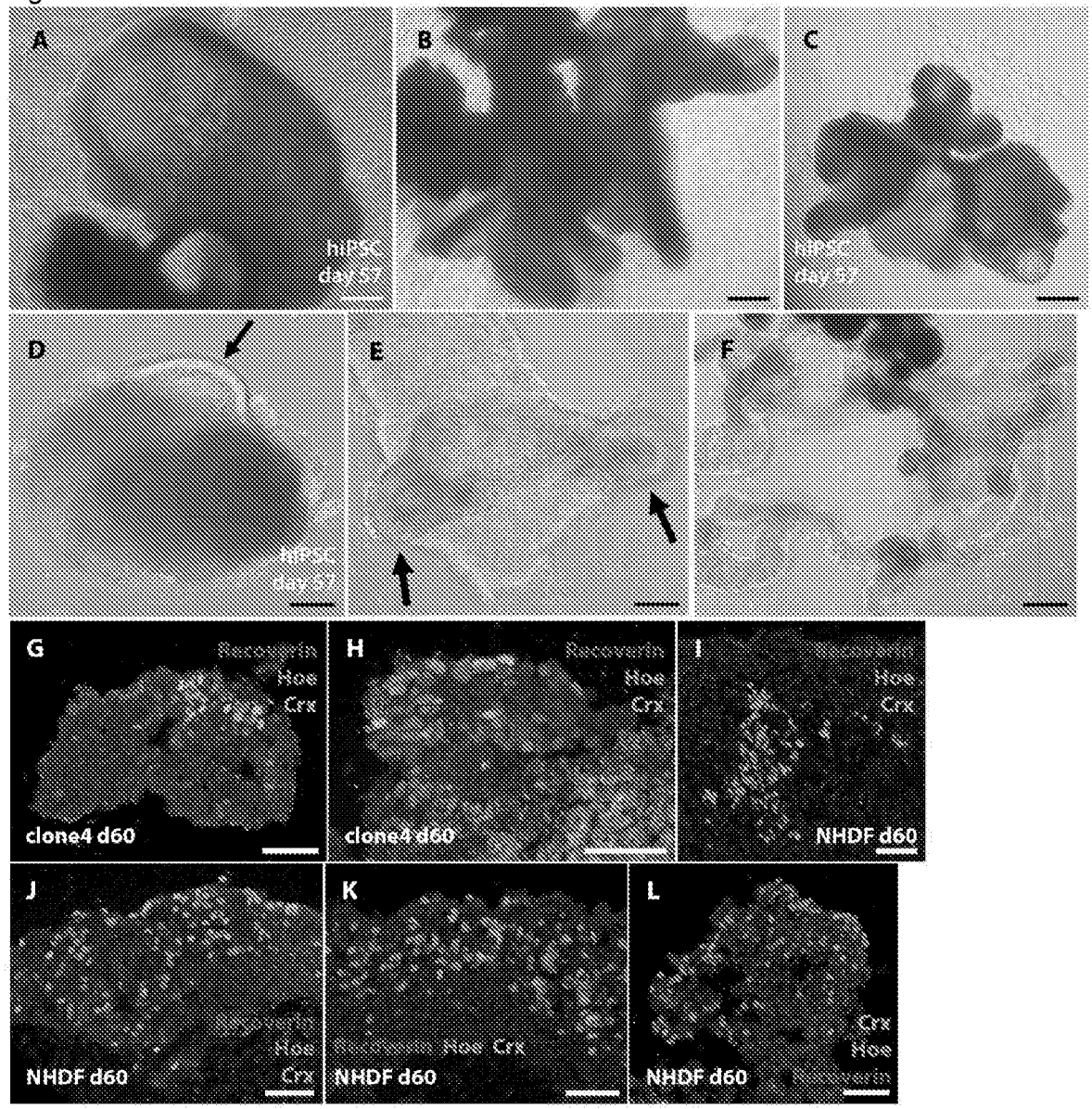
FIG. 8 shows examples of floating EBs derived from differentiating hiPSCs which displayed developmental features associated with neural and retinal development. EBs were derived from hiPSC clones 4 (A-C) and NHDF (D-F). The examples shown were differentiated under minimal (no B27, panel D), control (A-C, E) or PR-induction culture conditions (F). (A-C) Expansive sheets of proliferative neuroepithelium were evident in culture, in addition to phase bright neural retinal tissue (D) and bilateral optic vesicle-likestructures (panel E). (F) Expanding neuroepithelium was also observed to form elongated tissue structures which extended many millimetres in 3D culture. (G-L) Examples of retinal cells arising from hiPSC cultures on day 60 of differentiation which were expressing the photoreceptor marker Crx and (H, J) Recoverin. Scale bars; A-C=200 µm, D-F=100 µm, G-L=50 µm
Figure 9:
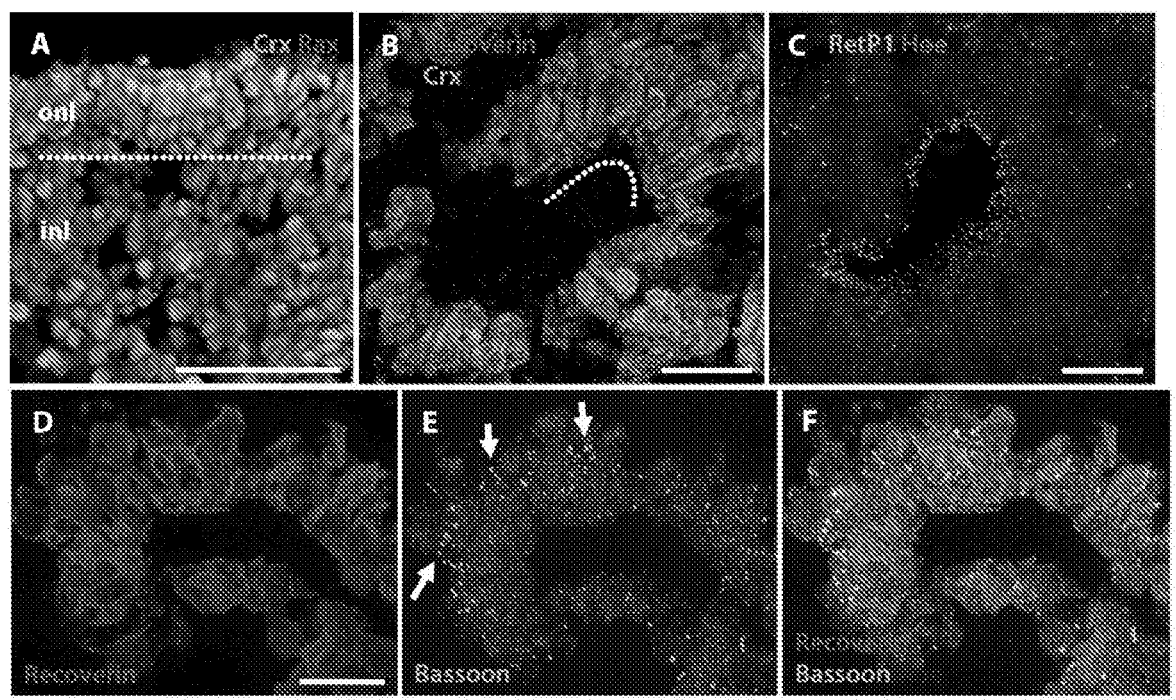
FIG. 9 shows immunostained sections of EBs that had been treated with IGF-1 for 90 days. While the correct laminar orientation of retinal cells, such as apically positioned photoreceptors, was most commonly found under IGF-1 treatment (A), in some cases photoreceptors were found to reside in the innermost layer of rosette-like structures (B-F). (B, D, F) Recoverin and Crx immunopositive photoreceptors typically aligned together to form a radially arranged layer (depicted by the dotted line in B) and showed immunoreactivity for (C) rod opsin (RetP1) and (E, F) Bassoon. Scale bars; B,C=25 µm, D=20 µm.
Figure 10:
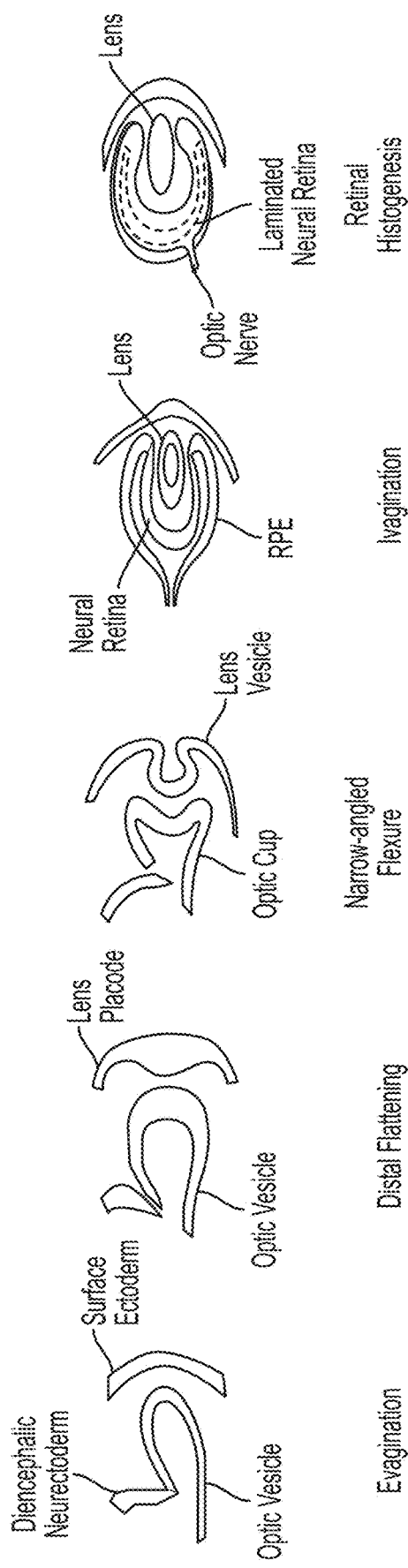
FIG. 10 shows a schematic presentation of retinal histogenesis which is recapitulated during murine esc differentiation resulting in formation of optic cup which is able to differentiate into a fully stratified neural retina and RPE.
Figure 11:
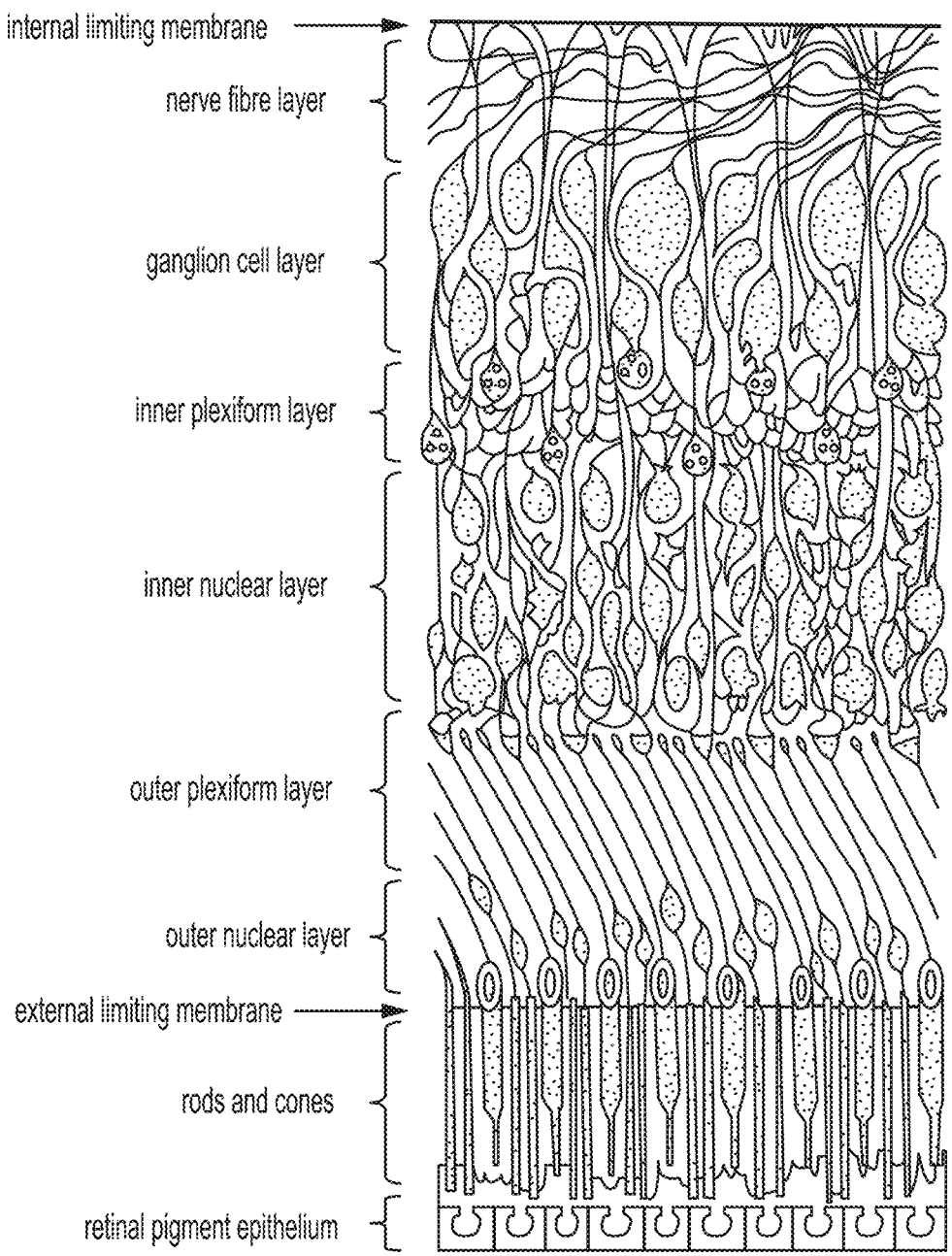
FIG. 11 shows a schematic presentation of the retina, which can be compared to the optic like cup structures obtained by the methods of the invention.

While hESC/hiPSC-derived embryoid bodies (EBs) differentiating under adherent 2D conditions form neural rosettes and optic vesicle-like structures containing retinal progenitor cells which give rise to photoreceptor-like cells and expanding sheets of RPE, the formation of complex structures that clearly resembled the optic cup was not obvious,[14] most likely due to the physical constraints of 2D culture conditions. In comparison, the culture of EBs in 3D suspension throughout differentiation (FIG. 1A) enabled the development of morphology reminiscent of the evaginating optic vesicle during embryonic development (FIGS. 1, 2A,F). These structures appeared under all differentiation conditions tested (FIG. 1B-G) whether those were minimal (in the absence of B27), control (in the presence of B27), IGF-1 supplemented cultures (B27+IGF-1) or all mitogens and growth factors supplemented cultures (which the inventors have termed photoreceptor [PR] induction conditions), but with different frequency. Phase bright tissue at the edge of EBs (FIGS. 2F, 8 D) developed to give rise to structures that resembled the optic cup and were most often associated with pigmented cells (FIGS. 1B-D, 3A, 4A, I). A small proportion gave rise to expanding sheets of cells which arose bilaterally (FIG. 1F, black arrows) then underwent folding to become more convoluted over time (FIG. 1G, 8 B, C, F) and were often accompanied by nearby distinct spherical areas of pigmentation (FIG. 1E-G, white arrows). In some cases polarised neuroepithelium occurred bilaterally, reminiscent of the early optic vesicles (FIG. 8E), or akin to the optic diverticula of the ventral forebrain prior to the closure of the neural tube (FIG. 8F). Differentiation of cells in low growth factor-containing Matrigel did not improve the efficiency of optic cup formation in this study (data not shown). Additionally, the inventors observed that utilising cells carrying a passage number higher than 45 significantly impeded optic cup formation from floating EBs (data not shown).

The Development of Neural Retina from Human Pluripotent Stem Cells Under Various Culture Conditions The inventors went on to investigate the internal composition of these optic cup-like structures arising from floating EBs. Under control conditions (in the presence of B27 but no IGF-1) on day 30, the inventors observed layered retinal neuroepithelium containing cells that were immunopositive for photoreceptor, horizontal, bipolar, amacrine and ganglion cell markers (FIG. 2A-D). Co-localisation of the presynaptic marker Syntaxin with HuC/D (staining amacrine and ganglion cells) and Islet1/2 (a ganglion cell marker) suggested that a putative inner plexiform layer was starting to form (FIG. 2D, E); however no mature morphology was observed and laminar organisation was variable between samples with most sampled optic cups containing a reverse laminar organisation [photoreceptors on the basal side (FIG. 2B) and other cell types (for example horizontal cells, FIG. 2C) on the apical side]. A very small number of the sampled optic cups achieved a proper organised structure by day 90, with retinal tissue occurring bilaterally (FIG. 2Gi, ii, Hi, ii) and showing typical polarisation with apically positioned photoreceptor cells (FIG. 2H, L) and basally located ganglion cells (FIG. 2I, M, N), indicating the formation of a multilayered neural retina. Yet, differentiating cells did not show outer segments despite staining with mature markers Opsin and Recoverin. Fascinatingly, folding and invagination of retinal neuroepithelium occurred in some (FIG. 1D, 2O) but not all examples; in fact many (including the example shown in FIG. 2F-N) went on to develop RPE and laminated retinal tissue without invagination taking place (FIG. 1B).

Figure 3:
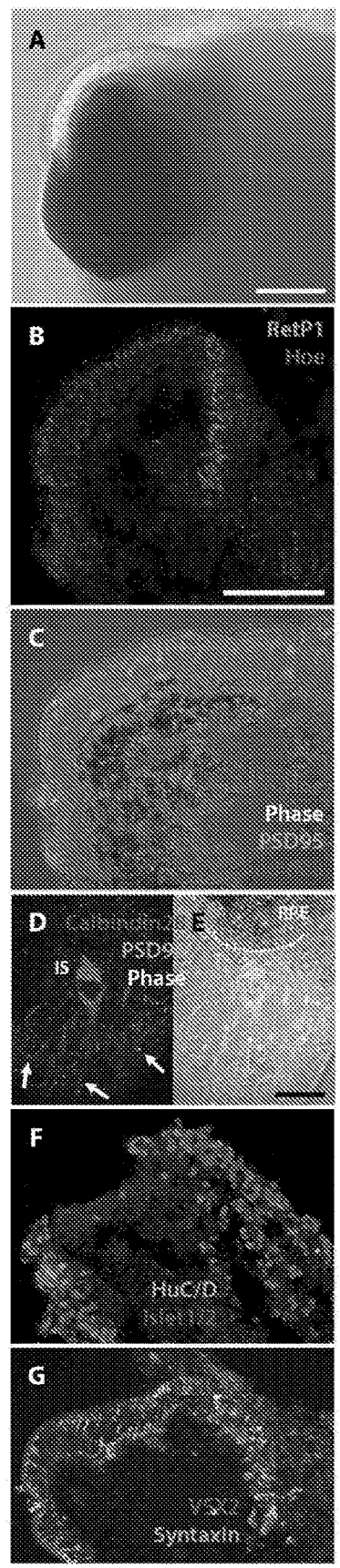
FIG. 3 shows differentiation of EBs under PR-inducing conditions promoted the morphological maturation of photoreceptors within developing retinal neural tissue. (A) EBs differentiated under PR-induction conditions for 40 days developed optic cup-like structures containing an anterior region of phase bright neural tissue and adjacent pigmented cup. Retinal neural tissue contained photoreceptor cells that expressed mature markers (B-E) and displayed ellipsoid cone inner and outer segment-like structures (D) that co-localised in the correct orientation with RPE cells (E) and expressed PSD95 on their axon terminals indicating synaptic formation with adjacent cells (D, E). In some cases, as demonstrated here, ordinarily basally positioned amacrine and ganglion cells were abnormally located at each side of developing apical retinal tissue (F, G), but this did not seem to affect the alignment or morphological maturation of adjacent photoreceptors (C-E). (F, G) The association of syntaxin staining with amacrine and ganglion cell markers indicates the structural formation of an inner plexiform layer. Scale bars; A=100 µm, B=50 µm, E=20 µm.

Human perifoveal and peripheral cones (excluding short wavelength cones) stain with Calbindin-D 28k (Calbindin 28). Exposing floating EBs to PR-induction conditions (exposed to all mitogens and growth factors, FIG. 3) enabled the production of photoreceptor cells to occur much earlier (within 40 days) than under control conditions (with mature cell types arising between days 60-90), as detected by their Rhodopsin and Calbindin 28 expression (FIG. 3B-E). Photoreceptors were aligned along a thick outer layer (FIG. 3B, C) and cone photoreceptors developed ellipsoid inner- and outer segment-like structures that co-localised with RPE cells, and expressed PSD95 on their axon terminals, indicating the formation of glutamatergic synapses with adjacent cells (FIG. 3D, E). In this example, developing amacrine and ganglion cells were abnormally located to each side of the developing photoreceptor and pigmented layers (FIG. 3F), but this did not interfere with the alignment or morphological development of adjacent photoreceptors (FIG. 3C-E). The association of Syntaxin staining with HuC/D and Islet1/2 further confirms the identity of these cells and indicates the structural formation of an aberrantly placed inner plexiform layer (FIG. 3G), suggestive of abnormal retinal lamination under PR culture conditions.

The emergence of phase bright retinal neuroepithelium was rare in cells differentiated under minimal culture conditions without B27 (FIG. 8D); an organised and clearly stratified neural retina was never observed, even by day 90, indicating a crucial requirement for B27 in the culture media in formation of multi-layered retina, albeit at low occurrence as shown above.

Laminar Organisation and Emergence of Mature Retinal Phenotypes within Optic Cups Derived in the Presence of IGF1

Figure 4:
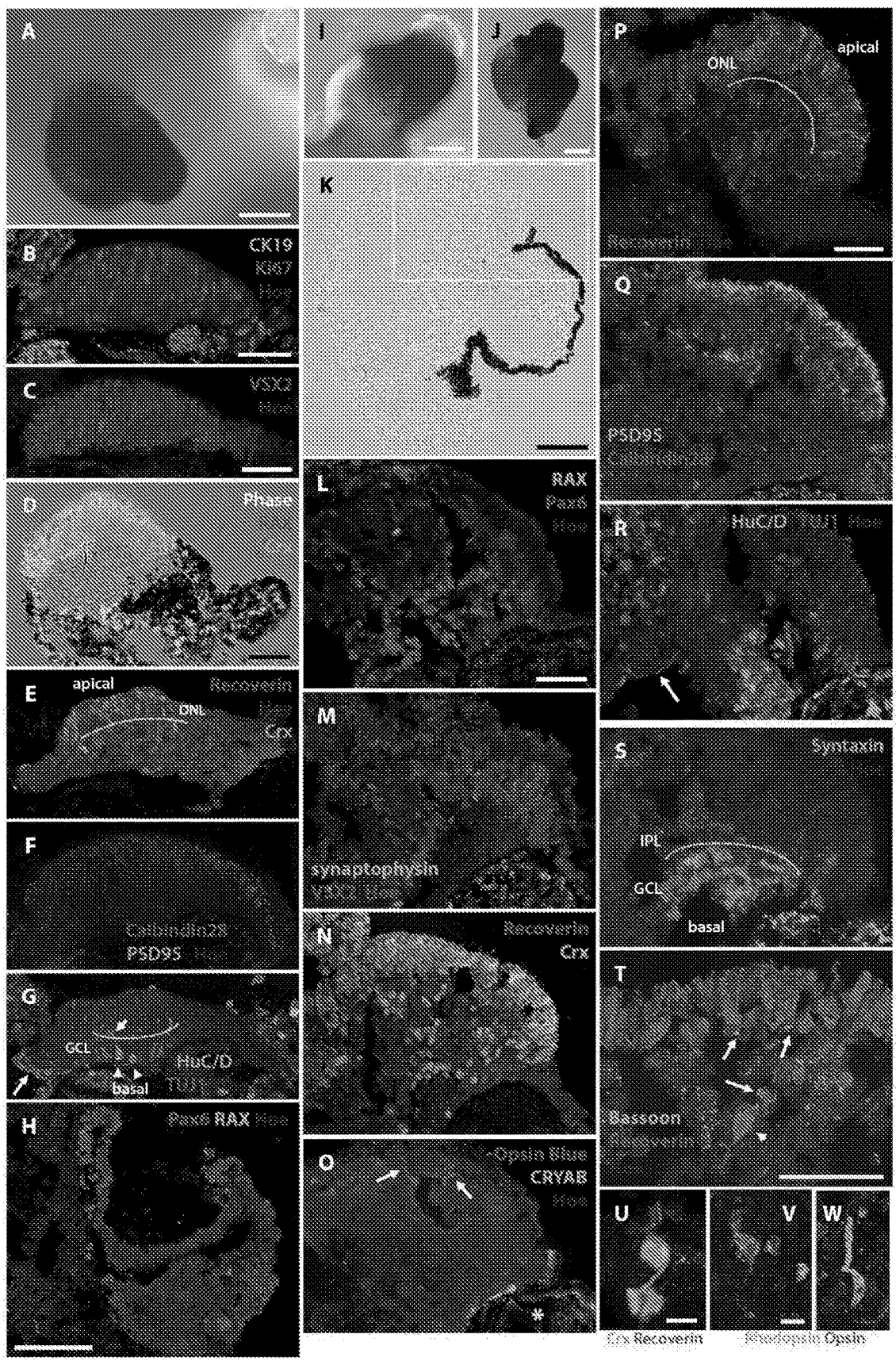
FIG. 4 shows treatment of differentiating cells with IGF-1 orchestrated the formation of organised laminated neural retinal tissue containing multiple retinal phenotypes. (A, I,J) Phase micrograph examples of developing optic cups from hESCs under IGF-1 treatment in vitro and corresponding sections through these tissues following immunofluorescent histochemistry. (A-G) An example of developing retinal tissue which still contained numerous proliferative retinal progenitors throughout the tissue depth on day 90 as indicated by Ki67 (B) and VSX2 (C) and therefore more immature photoreceptor morphology (E). This was rare at day 90, with most examples exhibiting greater numbers of postmitotic cells. Nonetheless, Crx+ cells existed along the apical edge of the tissue (D, E) and were associated with Calbindin28 staining (F), indicating the position of the future outer nuclear layer (ONL, indicated by the dotted line in E). Developing ganglion cells were found to reside at the basal side and extended processes into the retinal tissue (G, arrowheads) and along the basal surface forming a primitive nerve fibre layer (G, arrow), indicating the site of the future ganglion cell layer (GCL, indicated by the dotted line in G). (H) Invagination and folding of a hESC-derived optic cup forming two distinct layers stained with Pax6 and RAX. An example of an optic cup at day 39 (I) and day 57 (J) of development and sections through this structure at day 90 (K-W). (L-S) Enlarged area represented by the dotted line in (K). (L) Pax6+ cells were situated towards the basal aspect and (M) VSX2 medially with synaptophysin staining on the apical edge. Crx+(N), opsin blue (O) and recoverin (N, P) immunopositive cells were found on the apical side of developing retinal tissue, and on the internal surface of retinal rosettes (O). Recoverin and Crx immunopositive photoreceptors typically formed a radially arranged ONL (dotted line, panel P). (Q) The apical processes of photoreceptors stained with PSD95 and Calbindin28, with some staining also observed in inner processes. (R) Ganglion and amacrine cells were basally located and co-localised with syntaxin staining (S) indicating the region of the future GCL and inner plexiform layers (IPL, indicated by the dotted line in panel S). Apically located radially aligned Recoverin+ photoreceptors expressed Bassoon at their terminals (T) and exhibited morphology typical of maturing photoreceptors including the emergence of outer segment-like structures (U-W). Scale bars; V=10 µm, U=20 µm, B-D,L,P,T=50 µm, A,H,I,K=100 µm, J=200 µm

Immunostaining IGF-1 treated EBs on day 90 revealed structures similar to the developing neural retina (FIG. 4). Very few examples of arising neural retina appeared immature at this stage, characterised by a large number of proliferating cells and retinal progenitors as detected by Ki67 and VSX2 (FIG. 4A-C). In one instance, a clear optic cup bilayer was observed which expressed Pax6 throughout, but did not yet contain any photoreceptor cells (FIG. 4H). On day 90 of differentiation, the majority of sampled IGF-1 treated optic cups displayed laminar organisation, with a medial band of retinal progenitors (FIG. 4L, M) and an outer layer of Crx and Recoverin immunopositive photoreceptor cells (FIG. 4L-T). The results show that in the early stages $Crx^+$ cells can be positioned throughout the early developing retinal tissue (FIG. 4E), but become apically positioned along with the onset of Recoverin expression (FIG. 4N). While the inventors have previously observed that photoreceptors emerging under adherent 2D conditions do not survive over long term culture,[14] those differentiating in suspension and in the presence of IGF-1 survived and demonstrated further maturation for up to 90 days, the latest time point tested. Photoreceptor cells typically aligned side-by-side to form a radially arranged apical layer (depicted by the dotted line in FIG. 4P), strongly expressing PSD95 at their apical surface (FIG. 4Q). Inner retinal neurons were identified towards the basal surface and developing ganglion cells projected their axons along the presumptive nerve fibre layer (FIG. 4R, arrow). Syntaxin staining confirmed the presence of developing inner plexiform layer (FIG. 4S). Photoreceptors also expressed Bassoon on their terminals, indicating the formation of ribbon synapses (FIG. 4T, arrows). Photoreceptor cells exhibited inner and outer segment-like structures following immunostaining for mature photoreceptor markers (FIG. 4U-W).

While IGF-1 treatment enhanced the formation of laminated neural retinal with apically placed photoreceptors (FIG. 9A), a minority of differentiating EBs contained internal cell rosettes exhibiting a central hollow lumen surrounded by developing retinal tissue at varying stages of development. In such examples, $Crx^+$ cells were found surrounding the lumen (inverted apical surface, FIGS. 4O, 7G, 9B) and $HuC/D^+/TUJ1^+$ cells (putative ganglion cells) were found around the periphery (inverted basal surface) of retinal rosettes (FIG. 7H), akin to results previously reported.[13, 18] Even in inverted form, developing photoreceptors expressed rod Opsin towards the lumen and Bassoon at their terminals (FIG. 9C-F). Synaptophysin staining of processes was also detected on the luminal surface (FIG. 7F, G). A similar number of rosettes were also seen under control conditions, but they did not express mature photoreceptor markers, nor Bassoon or Synaptophysin.

TEM analysis of differentiating cells (FIG. 6A-I) revealed a high proportion of neurofilament-containing cells and pigmented cells which featured cilia, some of which demonstrated polarised location of melanosomes (FIG. 6C) indicating maturing RPE cells. Differentiating cells developed cilia and inner segment-like regions of cells expressed a single basal body complex and centriole (FIG. 6E, arrows), indicating the development of the photoreceptor connecting cilium. Although developing photoreceptor cells exhibited outer segment-like cell membrane protrusions linked to the soma by a thin connecting cilium-like structure (FIG. 6F-H), the identification of outer segment disk-like structures (FIG. 6I) was rare.

Formation of Accessory Eye Structures

Figure 7:
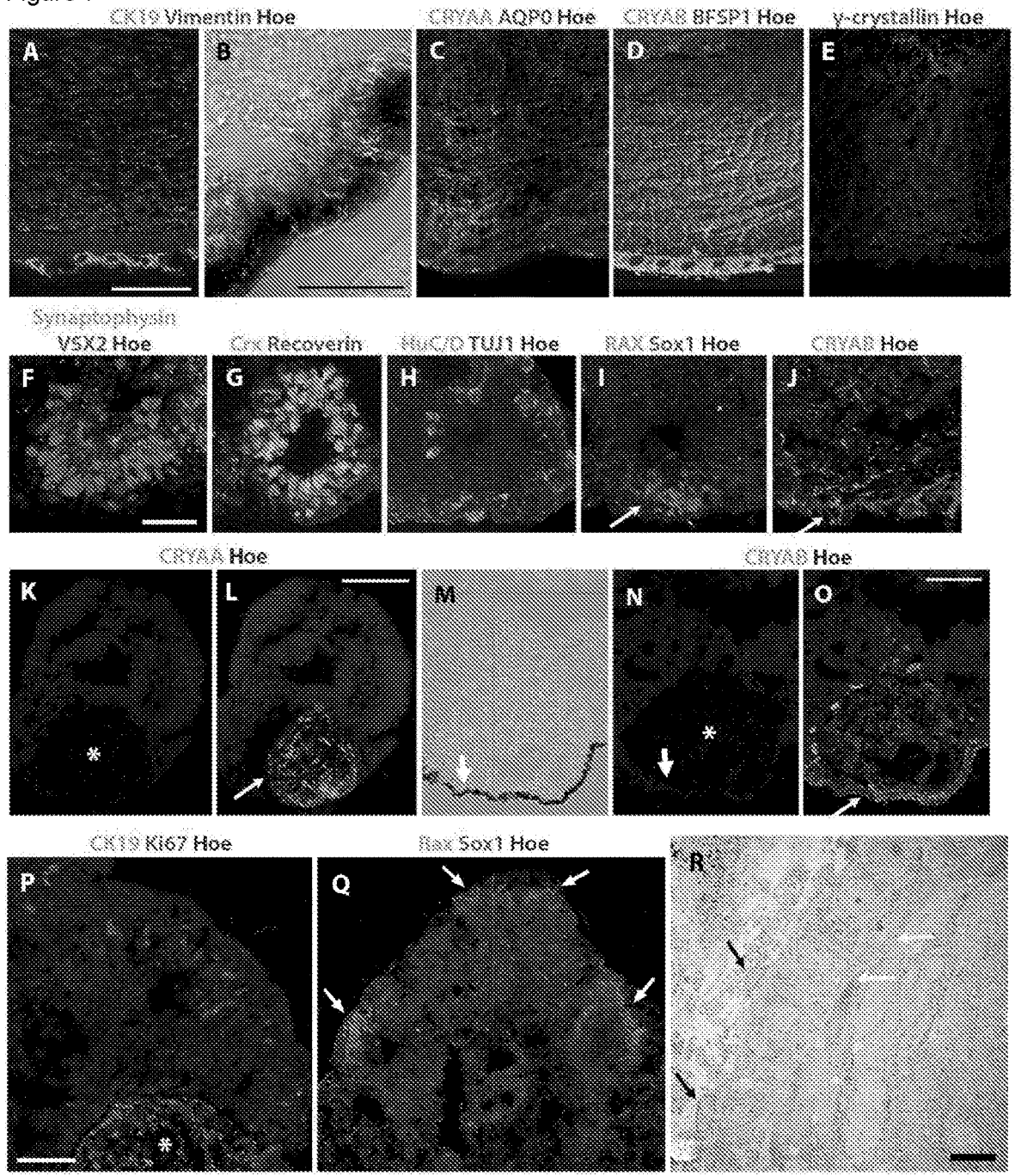
FIG. 7 shows IGF-1 treatment facilitates the emergence of ocular accessory structures alongside retinal tissues. (A-E) Sections through a 12 week developing foetus cornea (A), pigmented ciliary margin (B), and lens (C-E) stained for lens (CRYAA, CRYAB, γ-crystallin, AQPO, BFSP1) and corneal epithelial markers (CK19, vimentin). The pigmented ciliary margin (panel B) was also immunopositive for vimentin and CK19. (F-J) Serial sections through an EB in the region of a retinal rosette showing the medial location of retinal progenitor cells (F), internally residing photoreceptors (G) and superficially positioned ganglion cells (panel H). Photoreceptor terminals are stained with synaptophysin towards the inner surface of the rosette (F). Superficial regions of Sox1 (I) and CRYAB (J) immunostaining was often observed adjacent to developing retinal tissue close to the surface of the EB, indicating the emergence of the lens vesicle at the exposed side. (K, L) In a rare example under control conditions adjacent to developing retinal tissue, a region lacking nuclei (asterisk) was immunopositive for the lens marker CRYAA. This was observed more frequently in IGF-1 treated cultures (I, J, M-O). (M-O) Serial sections through an EB showing an area lacking nuclei stained with CRYAB and lined by a layer of pigmented cells (arrows) on the surface, which appear to be pigmented ciliary margin cells arising in close apposition to developing lens. (P) Very few proliferating cells remained in neural retinal tissue by day 90 of IGF-1 supplemented differentiation as observed with Ki67 staining. Cells adjacent to retinal tissue are stained with the corneal marker CK19 (asterisk). (Q) Superficial areas of Sox1 expression in EBs often occurred bilaterally (arrows). (R) TEM analysis revealed structures resembling developing corneal tissue comprising of deeper corneal layers contained by a band of basal cells (white arrows) and surrounded by superficial cells (black arrows). Scale bars; A,B,F,P=50 µm, L,O=100 µm, R=10 µm.

The inventors observed that regions of differentiating cells adjacent to developing RPE and retinal tissue were immunopositive for markers of accessory structures of the eye (FIG. 7). Sox1 is expressed in the lens vesicle shortly after the ectoderm gains a lens-forming bias, but is not found in the neural retina. Sox1 is also co-expressed with RAX in the neural epithelium of the adjacent diencephalon. Indeed, in neural rosettes containing retinal progenitors, photoreceptors and ganglion cells arising in IGF-1 supplemented cultures (FIG. 7F-H), the inventors observed that the portion of the rosette found towards the surface of an EB was often RAX negative and Sox1 positive (FIG. 7I), indicating a lens forming bias in these cells. This superficial region of RAX$^-$/Sox1$^+$ cells was observed only in IGF-1 treated cultures, and was often observed to arise bilaterally across EBs (FIG. 7Q, arrows). Consolidating this result, the inventors found superficial expression of the lens-specific Crystallin alpha B (CRYAB) alonsgside RAX$^-$/Sox1$^+$ regions (FIG. 7J), indicating that the signals necessary for formation of the early lens were present in differentiating hESCs treated with IGF-1 and that this was associated with retinal tissue formation. Pigmented cells themselves were sometimes CRYAB immunopositive and surrounded a region of tissue which contained fewer cell nuclei than surrounding regions (FIG. 7M-O, asterisk), indicating the enucleation of lens cells similar to that which occurs during development. It is possible that these CRYAB positive pigmented cells represented the presence of anterior pigmented ciliary margin cells in the cultures, which arise anatomically adjacent to the lens. Moreover, the inventors observed cells immunopositive for corneal progenitor cell marker, CK19 (FIG. 7A) and corneal epithelial-like structures in TEM micrographs (FIG. 7R) comprised of a core of cells forming a corneal-like concentric pattern, encased by a band of basal cells (white arrows) and surrounded by superficial cells (black arrows). Therefore, in the presence of IGF-1 additional ocular structures resembling corneal epithelial cells and lens vesicle can arise in vitro alongside the developing neural retina.

Electrophysiology

Figure 6:
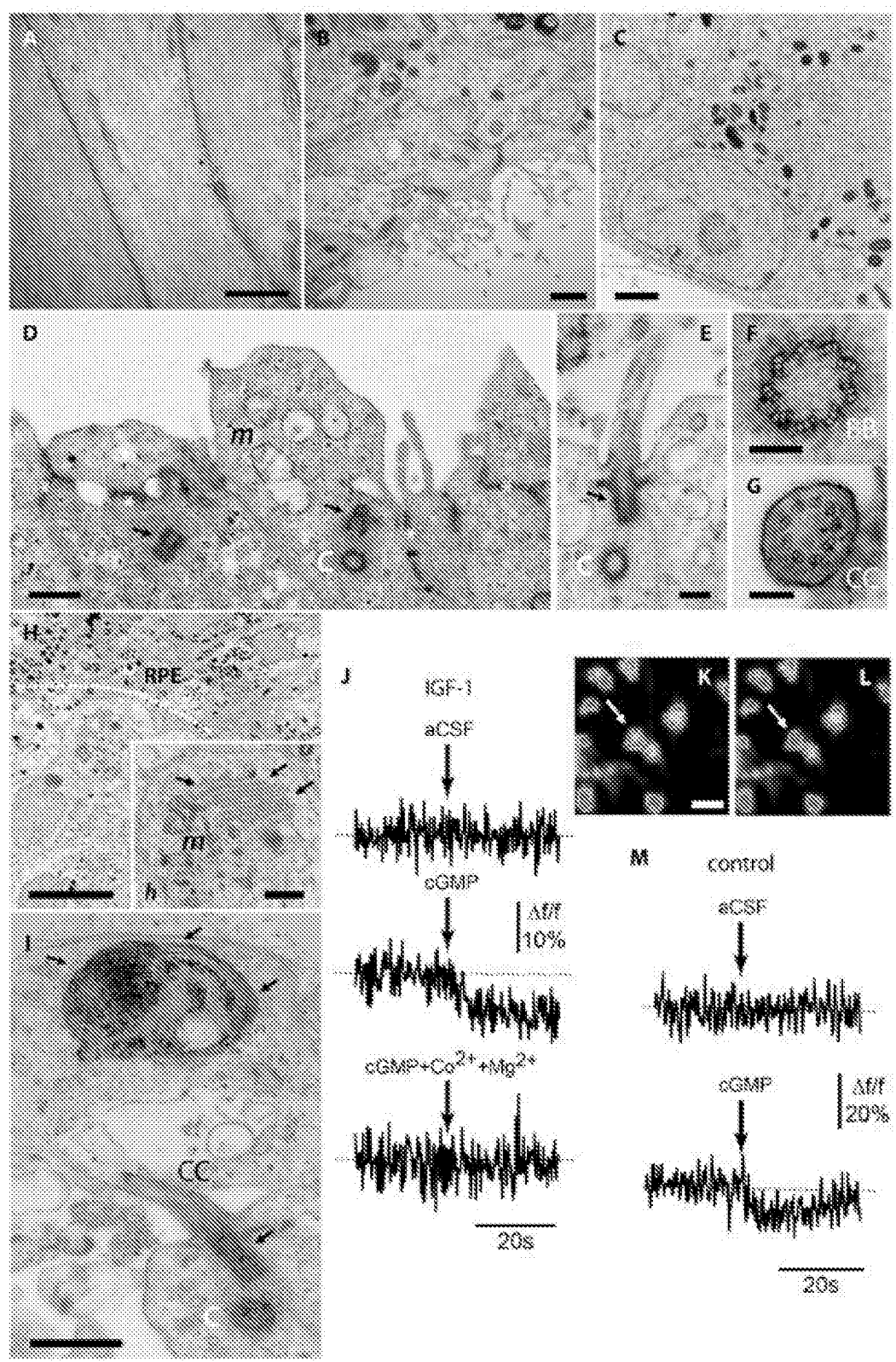
FIG. 6 shows TEM analysis of hESC-derived cell types and electrophysiological analysis of photoreceptors. (A-I) Ultrastructural analysis of differentiating hESCs treated with IGF-1. (A) Optic cup-like structures contained neural cells with prominent neurofilament and (B, C) pigmented cells which expressed cilia and (B) showed polarisation of melanosomes (C). (D) An outer limiting membrane was observed (white asterisks) alongside developing photoreceptor cells which exhibited mitochondrion-rich (m) inner segment-like membrane protrusions adjacent to photoreceptor-specific microtubule arrangements (D-G), revealing the presence of the photoreceptor centriole, 'C' (D,E), a clearly identifiable 9×3+0 basal body complex, 'BB' (D-F, I) and 9×2+0 connecting cilium, 'CC' (E,G,I). (H, I) The examination of photoreceptor cells developing adjacent to a layer of RPE (demarcated by the white dotted line) revealed ultrastructural features (H, asterisk and h,l arrows) similar to nascent outer segment discs that were found in close proximity to mitochondrion (m). (I) These structures were present alongside a single cellular centriole (CI basal body complex (arrow) and connecting cilium ('CC'), indicating the development of the photoreceptor connecting cilium. (J, M) Raw traces of cGMP-induced fluorescence changes in individual cells labelled with Fura2-AM, expressed as percentage change from baseline fluorescence in IGF-1 treated (J) and control cells (M) on day 45 of differentiation. The traces show changes in fluorescence when exposed to a 50 µl aCSF puff (top trace) and cGMP puff delivered at the time indicated by the arrow. In photoreceptor cells cGMP triggers an increase in calcium influx, reflected by a decrease in fluorescence, whereas aCSF has no effect. The fluorescence images (K, L) to the right of (I) illustrate the same cell (indicated by a white arrow) together with surrounding cells in the culture represented in false fluorescence colours before (averaged during 10 seconds; top image) and during (averaged during 20 seconds; bottom image) cGMP application. (J) The calcium response to cGMP (middle trace) disappears in the presence of cobalt chloride (2 mM) and magnesium chloride (3 mM) (and no calcium chloride) in the perfusate (lower trace). Scale bars; A,D,I=500 nm, B=1 µm, C,h=2 µm, E=200 nm, F,G=100 nm, H,K=10 µm.

In order to determine whether developing photoreceptors contained the machinery necessary for transduction, the inventors plated differentiating EBs onto poly-L-ornithine and laminin-coated 6 well plates for 15 days prior to optical recording using calcium imaging. Membrane disks in the outer segment of native photoreceptors contain a photopigment (for example the rod-specific pigment rhodopsin consists of opsin+retinal), and the cell membrane in outer segments contains cyclic guanosine monophosphate (cGMP)-gated cationic (sodium and calcium) channels. In the dark, cGMP levels are high and the photoreceptors are maintained in a depolarised state via influx of Na$^+$ and Ca$^{2+}$ through these cGMP-gated channels which are in an open state. Exposure to light causes the retinal part of the photopigment to isomerise to trans-retinal, leading to activation of multiple G-proteins and phosphodiesterase 6 which in turns degrades cGMP, resulting in closure of the channels and membrane hyperpolarisation. To test if the hESC and hiPSC derived photoreceptors respond in a similar manner, on day 30, 45 and 60 of differentiation, cells were exposed to flashes of red, green, blue or white light, or to membrane-permeable 8-br-cGMP. As 8-br-cGMP opens the cationic (Na$^+$ and Ca$^{2+}$) channel associated with phototransduction, it triggers a Ca$^{2+}$ influx in photoreceptors known as the inward dark current. Loading cells with the fluorescent Ca$^{2+}$ indicator Fura-2 therefore enables the visualisation of changes in intracellular calcium associated with opening or closing of the cGMP-gated channel, with a decrease in fluorescence representing an increase in calcium influx. When exposed to 8-br-cGMP, IGF-1 treated cultures showed decreased fluorescence (FIG. 6J-L), indicating a cGMP-mediated increase in Ca$^{2+}$) influx. This effect was abolished when cGMP was delivered alongside the calcium channel blockers cobalt chloride and magnesium chloride in the perfusate (FIG. 6J). On day 45 of differentiation 24.1% (±7.8) of IGF-1 treated cultures were cGMP respondent, and this increased to 45.3% (±13.2) by day 90. A similar proportion of cGMP responsive photoreceptor cells were observed under control conditions (FIG. 6M) in accordance with the observation of photoreceptor cells in these cultures (FIG. 2H, J-L). The inventors were however unable to detect any response of photoreceptor cells to light stimulation, likely due to the rare formation of outer segment disks and difficulty in capturing these cells for electrophysiological analysis.

IGF-1 Pathway Signalling Plays a Key Role in Optic Formation and Survival

Figure 5:
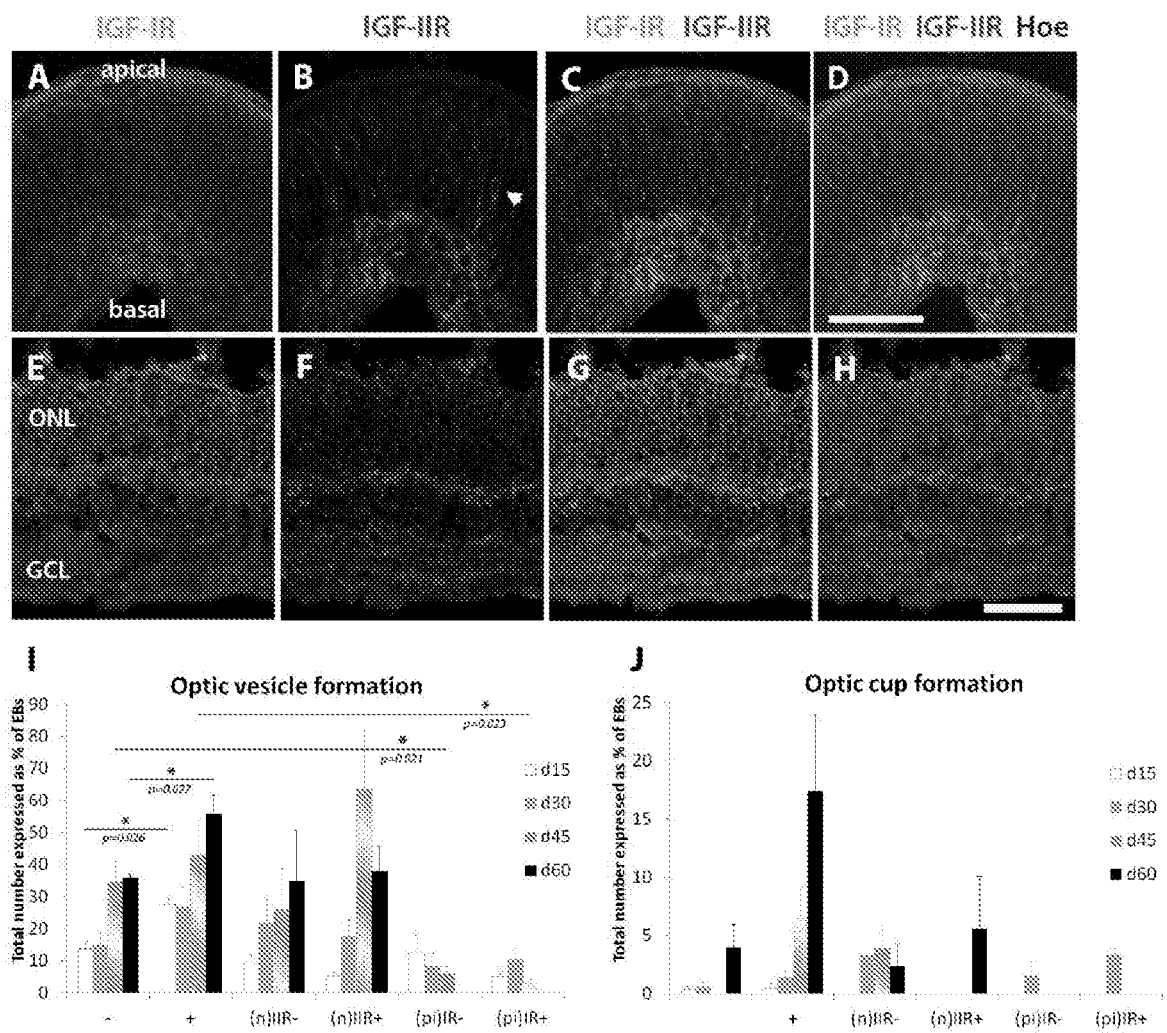
FIG. 5 shows interference of IGF-1 pathway signalling significantly inhibits optic vesicle and optic cup formation. (A-H) The expression of IGF-IR and IGF-IIR in (A-D) human fetal retina at 12 weeks of development and (E-H) adult human retina. IGF-IR expression was visualised in the neuroblastic layer and apical surface of the developing retina, while its expression in the adult retina was localised to photoreceptors in the ONL. IGF-IIR clearly localised to the neuroblastic layer in developing retina and the GCL, IPL and OPL in adult retina. (I, J) Treatment of differentiating EBs with IGF-1 resulted in a higher frequency of optic vesicle (I) and optic cup formation (J). Pharmacological inhibition of the IGF-IR ((pi)IR) both in the absence ((pi)IR−) and presence ((pi)IR+) of IGF-1 significantly reduced the formation of optic vesicles and optic cups, and did not permit the survival of EBs past 50 days of differentiation. Neutralisation of the IGF-IIR ((n)IIR) did not replicate this effect, implicating the IGF-1 signalling pathway as an important mediator of retinal development and survival. * indicates statistical significance, $P<0.05$

Retinal photoreceptors express IGF-1 receptors (IGF-IR) [22] and inclusion of IGF-1 in the differentiation media significantly increased the frequency of optic vesicle formation from differentiating hESCs FIG. 5I). In IGF-1 treated populations by day 15 optic vesicle formation was double that of control levels, suggestive of a critical role for exogenous IGF-1 in the very early stages of differentiation. A second wave of enhancement in optic vesicle and optic cup formation was observed at day 60 with IGF-1 treated cultures showing a 4-fold increase by day 60 (3.9% of control vs 17.4% of IGF-1 treated EBs, FIG. 5J).

To confirm the contribution of the IGF-1 signalling pathway in this process, the inventors differentiated cells in the presence of a pharmacological inhibitor of the IGF-IR (pi(IR)) or a neutralising antibody directed against the IGF-II receptor, IGF-IIR ((n)IIR), in the presence (+) or absence (−) of IGF-1 supplementation (FIG. 5I, J). Inhibition of IGF-IR significantly reduced optic vesicle production from differentiating EBs at day 45, both in the absence ((pi)IR−) and presence ((pi)IR+) of IGF-1 (p=0.021 and 0.023, respectively). Optic cups were undetectable in (pi)IR cultures on day 45 and while other experimental groups continued to thrive for the duration of the experiment, (pi)IR cultures did not remain viable after this time, indicating that endogenous IGF-IR signalling plays not only an important role in optic structure production, but also in cell survival, both in the presence and absence of exogenous IGF-1. Neutralisation of the IGF-IIR signalling pathway did not significantly alter the frequency of optic vesicle and optic cup formation formation, suggestive of the sole involvement of IGF-IR signalling in retinal differentiation from human pluripotent stem cells.

Experimental Methodology and Results—Discussion

The inventors have further investigated the conditions required for the formation of neural retina from human pluripotent stem cells and in doing so have revealed an important role for IGF-1. While the 3D culture of hESC/hiPSC-derived EBs can facilitate the development of optic cup-like structures containing RPE and neural retinal tissue under minimal and control culture conditions, this occurs at low frequency and often results in reverse and/or abnormal laminar organisation. The PR-induction media which contains a large number of mitogens, signalling agonists and antagonists enabled the early formation of photoreceptors, but did not achieve the levels of retinal laminar organisation and maturity observed in IGF-1 treated cultures. In comparison to all other conditions tested, the development of the optic vesicle, optic cup and laminated neural retina associated with emergence of adjacent RPE were observed with greatest frequency in cultures treated with IGF-1. Control cultures which incorporate B27 but not IGF-1 result in much lower frequency of optic vesicle and optic cup formation and do not result in generation of photoreceptor cells with outer segment-like structures which are easily observed in the presence of IGF-1. In addition, elimination of B27 from culture media abrogates the ability of hESC and hiPSC to form laminated neural retina in culture. Together these data suggest that combined application of B27 and IGF-1 with a minimal culture media promote and direct the differentiation of human pluripotent stem cells towards generation of laminated retina containing mature photoreceptors.

The inventors had previously reported the loss of photoreceptors from their adherent cultures between days 45 to 60 of differentiation, yet their recent work has revealed that this is not the case for floating EBs and that photoreceptors in these IGF-1 treated cultures continue to arise and can mature up to day 90 of differentiation, the latest time point studied. One possibility is that well aligned photoreceptors and a stratified retina with other secondary neurones as observed in the IGF-1 treated cultures can help to maintain viability by mimicking a native retinal microenvironment which is lacking in adherent 2D derived retinal differentiation protocols. However, this may not be the only determining factor as emerging retinal laminae within optic vesicular structures differentiating from hESC or hiPSC derived from other groups have been reported to lose their integrity over time.[15] In contrast to those studies, the inventors have observed however that photoreceptors arising in 3D cultures were maintained over long term culture and continued to mature, alongside other associated retinal cell types. This observed higher viability could be due to presence of IGF-1 in the culture media as interference with IGF-1 signalling under these experimental conditions lead to loss of viability of retinal structures as early as day 45 of differentiation. Together these data suggest that IGF-1 is a critical player for the induction of eye field and eye cup from pluripotent stem cells and for the maintenance of viable photoreceptors within the laminated neural retina emerging during 3D differentiation process.

Developmental studies have shown that across the entire spectrum of signalling molecules required for eye specification in any model system, injection of IGF-1 in *Xenopus* embryos specifically promotes induction of ectopic eyes containing a typical multilayered neural retina, RPE and sometimes lens.[21] IGF-1 is largely produced by the liver, although a number of other tissues including those of the central nervous system can produce IGF-1 locally. Consistent with a role in retinal development, IGF-1 is higher in post-natal retina compared to adult retina. Most importantly, expression of the IGF-1 receptor is observed in the very early stages of optic cup formation in 28-32 day old human embryos and is subsequently restricted to the lens and RPE at 6 weeks of development. Addition of IGF-1 to the culture media of differentiating hESC has been shown to significantly increase the number of RPCs, however its effects on optic vesicle and cup formation until now had not been reported.[5] As retinal differentiation proceeds, IGF-1 expression is observed in postmitotic retinal precursors which are in the process of differentiating into cones, as well as in the inner segments of photoreceptors promoting cone and rod survival. This is supported by studies in mice lacking insulin receptor substrate 2, an essential component of the IGF-1 signalling cascade, which show almost complete loss of photoreceptors by 16 months of age. IGF-1 is also observed in rod outer segments and has the ability to phosphorylate rod transduction, indicating that IGF-1 signalling may also be involved in light transduction. The expression studies described herein in human fetal and adult retina show a localised expression of IGF-IR in the developing outer nuclear layer; however a more widespread pattern of IGF-IIR in the plexiform and ganglion cell layer was observed, suggesting a more focal role for IGF-IR than IGF-IIR in the signalling pathway triggered by IGF-1. The expression pattern of these two receptors also fit well with signalling interference studies which show that inhibition of IGF-IR but not IGF-IIR reduce significantly the optic vesicle and cup formation and abrogate the viability of emerging neural retina in the 3D differentiation system. More importantly, this occurs both in the presence and absence of IGF-1, indicating that endogenous IGF-1/IGF-IR signalling is a key orchestrator in retinal induction from pluripotent stem cells.

Emergence of laminated retinal tissue in the IGF-1 treated 3D cultures is not proof of functionality for the residing photoreceptors and other retinal cell types developing therein. To obtain proof of cell functionality the inventors investigated synapse formation and photo-transduction capabilities. The results demonstrate clear PSD95 and synaptophysin staining indicating the formation of synapses and therefore the beginnings of an inner and outer plexiform layer in the hESC/hiPSC-derived neural retina, indicative of synaptic zones connecting photoreceptors with bipolars and ganglion cells, which has not yet been demonstrated in other work of this nature. IGF-1 may have enabled this to occur, as it is reported to activate molecules within neurons that help enable synapses to mature. The presence of other ocular-associated tissues in this study may be a contributing factor in enabling the more advanced photoreceptor maturation and the development of the outer segment-like structures which the inventors observed in their study. The formation of cone photoreceptors demonstrating inner and outer-like segments directly adjacent to retinal pigmented tissue under PR-induction conditions further demonstrates the incredible ability of human pluripotent stem cells to form neural retina that is correctly anatomically oriented. Additionally, inner retinal neurons were identified towards the basal surface and developing ganglion cells projected their axons along the developing nerve fibre layer. Syntaxin staining confirmed the presence of a developing inner plexiform layer. Furthermore, the expression of presynaptic marker, VGLUT1 which is essential for transmission of visual signals from photoreceptors to second- and third-order neurons was observed in a punctate pattern juxtaposed to the basal aspect of photoreceptors and the apical aspect of TUJ1-positive inner retinal neuronal processes, indicative of the formation of synaptic vesicles. A similar punctate pattern of expression localised adjacent to TUJ1-positive neuronal processes was also observed for Synapsin 1, suggestive of formation of conventional synapses between retinal ganglion cells and neurons of the inner nuclear layer.

Importantly the inventors also demonstrate that a proportion of hESC-derived photoreceptor cells express cyclic nucleotide gated (CNG) channels and are sensitive to cGMP stimulation in a similar manner to native photoreceptors, although the inventors were unable to detect any light responses in cells differentiated for up to 90 days. This could potentially be achieved by allowing additional maturation time in culture, and is currently under further investigation. Nonetheless, the presence of primitive outer and inner segment structures along with the expression of cGMP-responsive CNG channels demonstrates that these cells are undergoing continued development towards a functional photoreceptor cell.

During normal human development, the presence of synaptophysin in cone photoreceptor processes is visible around 12 weeks and is present in photoreceptor terminals by 16-17 weeks of gestation.[23] Cones are arranged into mosaics by 18-19 weeks of gestation and by 24-25 weeks exhibit an ellipsoid distal portion of their inner segment.[24] Syntaxin staining of the inner plexiform and nerve fibre layer is clear by 12 weeks of gestation and is present in amacrine and ganglion cells by 16-17 weeks. Taking this information from normal human development into account and linking this to what the inventors have observed in their cultures, the stage of maturation of the retinal tissue derived under IGF-1 treatment that the inventors have observed suggests they correspond to a gestational age of 17-25 weeks.[23, 24] This is surprising, given that the differentiation period was 90 days (~13 weeks), and suggests that certain aspects of normal development can be accelerated in vitro. This developmental time frame is faster than reported in a recent study which showed that generation of photoreceptor precursors was possible only after 13-18 weeks in culture media conditions which contained fetal bovine serum and a larger number of growth factors and signalling agonist/antagonists[15] Herein the inventors describe a simpler, more rapid and GMP-compatible method that lacks fetal calf serum and results in generation of more mature and stable photoreceptors within a shorter time frame.

TEM analysis of differentiating cells (FIG. 6A-I) revealed a high proportion of neurofilament-containing cells and pigmented cells which featured cilia, some of which demonstrated polarised location of melanosomes (FIG. 6C) indicating maturing RPE cells. A layer of adherents junctions demarcating the position of the outer limiting membrane was observed (FIG. 6D, asterisks) alongside developing photoreceptor cells which exhibited mitochondrion-rich (FIG. 6D, m) inner segment-like cell membrane protrusions and photoreceptor-specific microtubule presentations (FIG. 6D-G), confirming the presence of the photoreceptor centriole (FIG. 6D, E), basal body complex (FIG. 6D-F, I; a 9×3+0 arrangement) and connecting cilium (FIG. 6E, G, I; a 9×2+0 arrangement). The ultrastructural examination of photoreceptor cells developing adjacent to RPE revealed the presence of organised structures which may represent nascent outer segment discs (FIG. 6H, I), similar to that shown in the study by Zhong et al. [23]. The definitive identification of photoreceptor outer segments becomes much easier once the morphologically identifiable tall stack of outer segment discs has clearly formed. In our study, as in [23], the outer segment-like structures which have been identified are comparatively small organised stacks, which may represent the early emerging photoreceptor outer segment following the production of a minimal number of outer segment discs. Although it's difficult to distinguish early photoreceptor outer segments from other well-organised organelles, the topological proximity of these structures to the RPE (FIG. 6H) and their association with the presence of a single cellular centriole and connecting cilium (FIG. 6I), however, strengthens this notion, and indicates that photoreceptor cells derived from stem cells may demonstrate some capacity for outer segment disc formation and assembly. Importantly, these nascent outer segment disk-like structures (FIG. 6H/h, I) could be observed in the IGF-1 treated group only.

The inventors are not aware of any reports documenting the emergence of accessory structures associated with the neural retina during development, such as primitive lens or surface ectoderm, in studies of this nature. The inventors however observe that in the presence of IGF-1 these structures emerge alongside developing retina in this study, challenging paradigms of retinal development. While lens fiber cell formation is rarely seen in ectodermal explants not exposed to the optic vesicle, the neural retina and FGF can stimulate lens development, and the vitreous humor contains IGF-1 which has been shown to potentiate lens fiber differentiation by inducing pulses of crystalline gene expression in rat lens epithelial cells, indicating that this may have contributed to the formation of early lens that the inventors observed in IGF-1 treated populations. The emergence of neural retina from hESC/hiPSCs both with and without nearby lens cells in these cultures is an interesting result, given the ongoing debate surrounding the requirement of the lens in neural retinal formation. The inventors also observed the presence of RAX immunopositive cells within folded neuroepitheliel sheets of cells found adjacent to developing retina, indicating a ventral neural fate within these convoluted structures, such as diencephalic neural tissue, normally found adjacent to the eye field during normal development. This implies that not only lens and cornea, but other tissues normally found nearby to the developing eye are arising in parallel in vitro. This fascinating result clearly deserves further investigation.

The results herein suggest that 3D culture conditions results in development of optic cup-like structures containing RPE and neural retinal tissue. Addition of IGF-1 in the absence of any other growth factors increased the efficiency of optic cup-like structure formation as well as achieving a high level of retinal lamination accompanied by mature photoreceptor morphology and formation of other accessory eye structures. The simplicity of IGF-1 supplemented culture system and the ability to produce mature photoreceptors within a fully laminated retina, makes this an ideal system for future cell based replacement therapies as well as in vitro modelling of inherited retinal dystrophies.

Experimental Methodology and Results—Materials and Methods hESC/hiPSC Culture and Differentiation hESC (line H9, WiCell) and hiPSC lines Clone 4[25] and NHDF[26] were expanded and differentiated as previously described.[14] For IGF-1 treatment, cultures were differentiated in VNIM media[14] supplemented with recombinant human IGF-1 (5 ng/ml, Sigma) until day 37, then in basal Knockout serum-free media[14] with 10 ng/ml IGF-1 until day 90 (FIG. 1A). Control cultures were differentiated in parallel in the absence of IGF-1. Time-lapse capture of culture morphology was achieved using a BioStation CT (Nikon).

Immunocytochemistry and TEM

EBs were fixed over days 30-90 of differentiation and immunocytochemistry performed on cryostat sections as previously described.[14] Sections were reacted against a panel of retinal, lens and corneal-specific antibodies, listed in Table 1. Images were obtained using a Zeiss Axio Imager.Z1 microscope with ApoTome.2 accessory equipment and AxioVision software. For transmission electron microscopy (TEM) tissues were fixed in gluteraldehyde and processed by the Electron Microscopy Research Service at Newcastle University.

Electrophysiology

EBs were dark adapted for 24 hours prior to recording then loaded with Fura-2 AM (10 µM, Molecular probes/Invitrogen) for 45 min at 37° C. (95% $O_2$/5% $CO_2$) followed by perfusion (1 ml/minute) with oxygenated artificial Cerebrospinal Fluid (aCSF; 118 mM NaCl, 25 mM $NaHCO_3$, 1 mM $NaH2PO_4$, 3 mM KCl, 1 mM $MgCl_2$, 2 mM $CaCl_2$, 10 mM glucose) for one hour. Cells were exposed to 8-br-cGMP (cGMP, 1 mM, Sigma) in aCSF. Control recordings were performed with aCSF alone or with 8-br-cGMP in $CaCl_2$-free aCSF supplemented with calcium channel blocker Cobalt (II) chloride ($CoCl_2$, 4 mM, AnalaR) and 10 mM HEPES. Fluorescence was monitored using an inverted Olympus IX71 microscope and images (excitation 380 nm, 800 ms exposure) acquired using a Quantem 512SC camera (Photometrics) and MetaMorph Software (Molecular Devices). For each stimulation 20 seconds baseline activity was recorded. Fluorescence change was analysed using the formula % $\Delta l/l_o = (l_1 - l_o) \times 100/l_o$, where $l_o$ was the average cellular fluorescence during baseline activity and $l_1$ following stimulation. Significance was determined using a student's t-test (P<0.01).

IGF-1 Receptor Signalling Interference hESCs were expanded and differentiated as described. For interference of IGF-1 receptor signalling an IGF-IR-specific pharmacological inhibitor ([7 µM], AG1024, Stratech) was added to differentiation media for the entire differentiation period. To block/neutralise IGF-II receptor signalling, media was supplemented with goat IgG anti-human IGF-IIR antibody ([0.25 µg/ml], AF2447, R&D) throughout differentiation.

Alternative Modified Protocol—Retinal Differentiation of mTeSR1 Adapted Cells in 3D Differentiation Media to Prepare:
20%: DMEM:F12 (with L-Glutamine)+NEAA+P/S+B27 (1:50)+20% Knockout serum replacement (KOSR)+IGF-1 (5 ng/ml)
15%: DMEM:F12 (with L-Glutamine)+NEAA+P/S+B27 (1:50)+15% KOSR+IGF-1 (5 ng/ml)
10%: DMEM:F12 (with L-Glutamine)+NEAA+P/S+B27 (1:50)+10% KOSR+IGF-1 (5 ng/ml)
Serum-free: DMEM:F12 (with L-Glutamine)+NEAA+P/S+B27 (1:50)+N2 (1:100)+IGF-1 (10 ng/ml)

Control medium is prepared as above, without the addition of IGF-1.

Reagent Information:
DMEM:F12 (with L-glutamine): Life Technologies Cat # 10565-018
Recombinant human IGF-1: Sigma Cat # SRP3069
B27 supplement: Gibco Cat # 17504-044
N2 supplement: Gibco Cat # 17502-048

Method:
1. Enzymatically prepare EBs as described in 'Enzymatic method of EB production_mTeSR1 adapted cells'.
2. Collect EBs using a wide enough bore pipette (a 10 ml pipette is usually fine at early stages, but the use of a 25 ml pipette may be necessary at later stages) and add to a 50 ml Falcon tube. Allow the EBs to settle at the bottom of the tube.
3. Remove supernatant, gently add 10 mls differentiation media for each bacteriological dish of EBs collected, then transfer EBs to fresh bacteriological dishes (10 mls/dish). EBs are graded through differentiation media as follows:
Culture EBs for 5 days in 20% differentiation media
Followed by 4 days in 15%
Then in 10% until day 30
From day 30 onwards maintain EBs in serum-free differentiation media
4. Important: Change media every day until the media is clear (no floating debris), at which point, proceed to change half of the differentiation media every day (i.e. remove 5 mls spent media and replenish each bacteriological dish with 5 mls fresh media).
5. By day 30-40 of differentiation, if the media is still free of debris and not turning orange/yellow over the 24 hr feeding period, then change half the media every 2-3 days for the remainder of the experiment (at least 90 days).

Once the EBs stop shedding and the media remains clear overnight, instead of collecting the EBs into a Falcon tube I find it easier to simply remove the spent media from the bacteriological dish itself using a 10 ml pipette. To do this, tip the dish at an angle (making sure the EBs collect towards the bottom and are in some media so they do not dry out), rest one corner of the dish on its lid and carefully remove the media avoiding the EBs. Gently add the fresh media by flushing it from the top of the bacteriological dish, so as not to damage the EBs. This saves A LOT of plastic.

6. By day 60-70 of differentiation, if the media is still free of debris and not turning orange/yellow over the 24 hr feeding period, then change half the media every 2 days for the remainder of the experiment (at least 90 days).

Once the EBs stop shedding and the media is clear to, instead of collecting the EBs into a Falcon tube, simply remove the spent media from the bacteriological dish itself using a 10 ml pipette. To do this, tip the dish at an angle (making sure the EBs collect towards the bottom and do not dry out), rest one corner of the dish on its lid and carefully remove the media avoiding the EBs. Gently add the fresh media by flushing it from the top of the bacteriological dish, so as not to damage the EBs.

Additional Experimentation

Alternative Media Formulations

Figure 13:
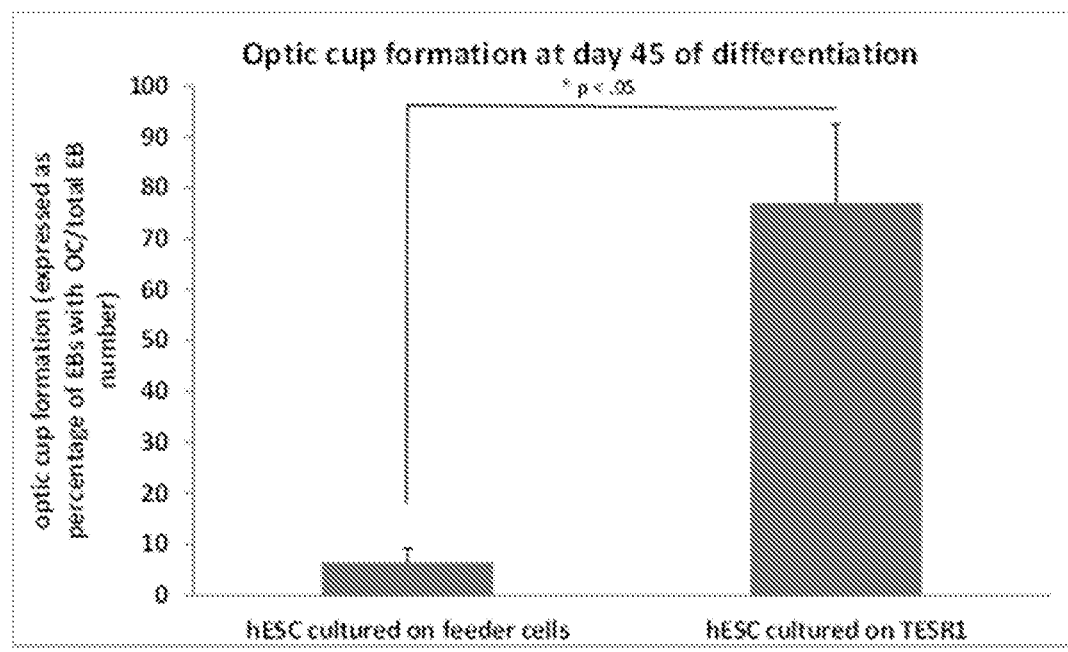
FIG. 13 shows adaptation of human pluripotent stem cells to mTeSR1 feeder free culture leads to a significant increase in formation of human optic cup structures in the presence of IGF-1.
Figure 14:
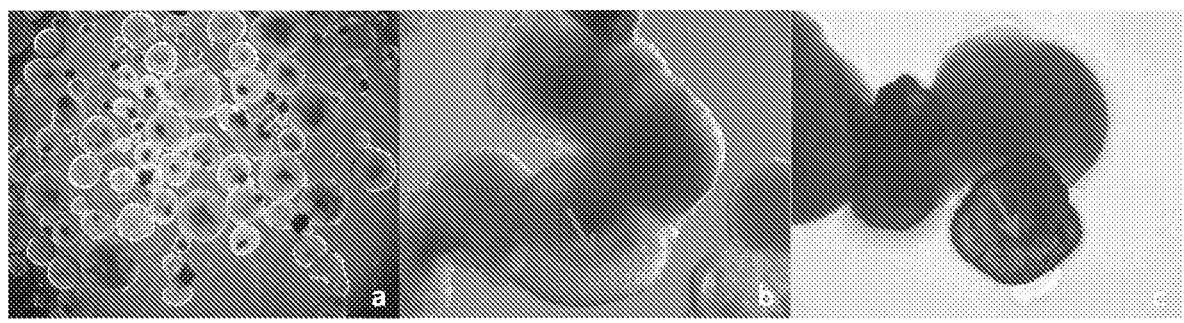
FIG. 14 shows examples of differentiating EBs from hESC that were expanded under mTeSR1 feeder-free conditions (panel a) containing evaginating neuroepithelium (panel b; blue arrow) and clear RPE patches (blue arrow, panel c) at day 33 of differentiation.

Human pluripotent stem cells were grown under feeder free conditions the effect of feeder free conditions on their differentiation potential to synthetic retina investigated.

mTeSR1 media (Stem Cell Technologies) is a highly specialised serum-free and complete media designed for feeder-free culture. Cells to this feeder-free technique and subjected to differentiation studies using the IGF-1 factor as discussed above. A very high and significant increase in formation of optic cup (OC) structures was observed as shown in FIGS. 13 and 14.

Modifications to the differentiation media (consisting of VNIM+KOSR+B27+N2+IGF-1) were also investigated by i) removing knock-out serum (KOSR); ii) increasing IGF-1 concentration; and/or iii) by adding 1% matrigel (MG), which has been shown to have a positive impact on differentiation of murine pluripotent stem cells to optic cup structures.

Figure 15:
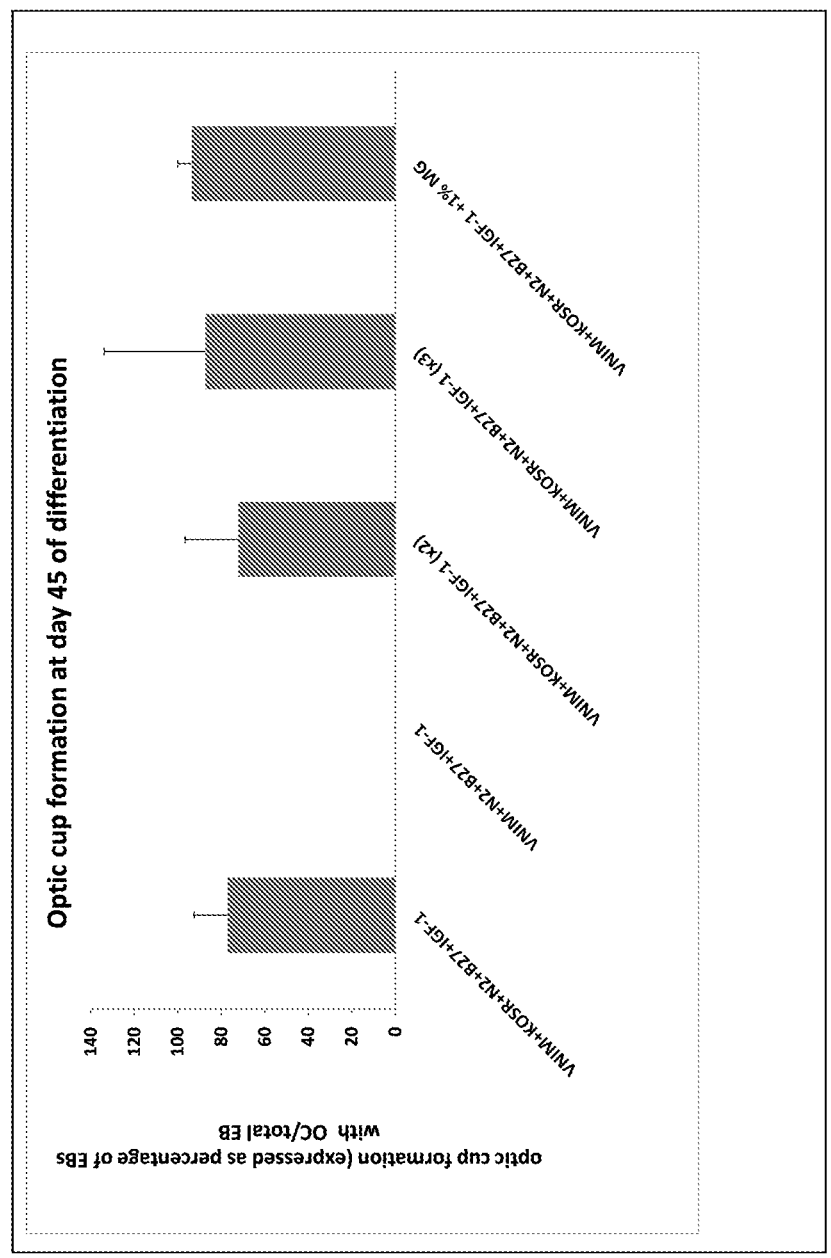
FIG. 15 shows removal of KOSR from the differentiation media abrogates the ability of hESC to form optic cups in vitro. VNIM-basal ventral neural induction media consisting of DMEM/Ham's F-12. ×2 and ×3 indicate a 2 and 3 fold increase in IGF-1 concentration respectively, MG=matrigel.

Whilst removal of KOSR from differentiation media completely abrogated formation of optic cups, addition of Matrigel or increasing IGF-1 concentration, did not cause any significant changes (FIG. 15).

Figure 16:
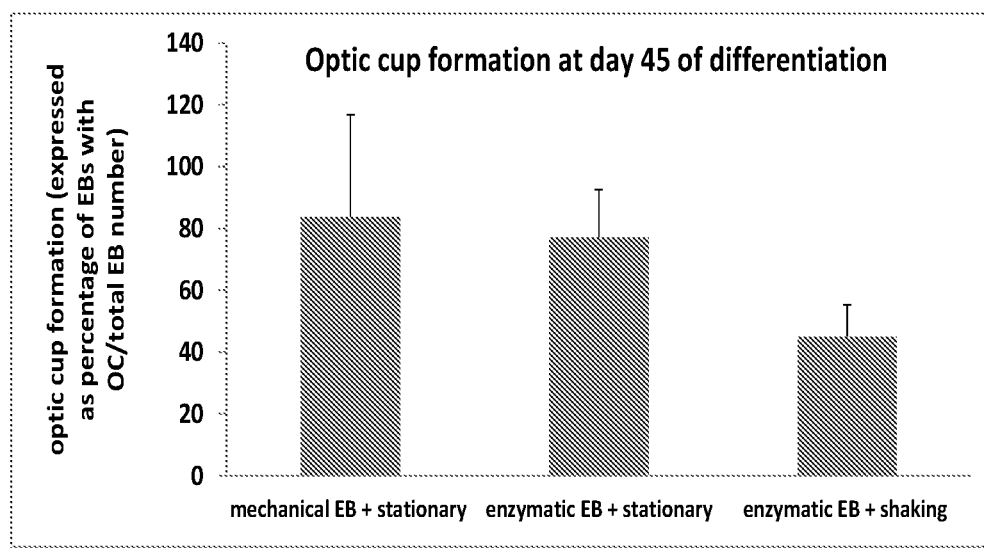
FIG. 16 shows the effects of EB formation and dynamics of differentiation conditions on the optic cup formation from hESC.

The mechanical way of making three dimensional embryoid bodies (EBs) was compared to an enzymatic method (FIG. 16). In addition, a comparison of static differentiation to a dynamic (shaking at low speed, 45 rpm) was made; however no significant differences were found (FIG. 16).

The data presented confirms that the most efficient optic cup formation is obtained by human pluripotent stem cells grown under mTeSR1 feeder free conditions, which are enzymatically treated to form 3D embryoid bodies and cultured under stationary conditions with VNIM+B27+N2+IGF-1 up to 90 days to generate synthetic retina.

Essential Media Components

Prior to differentiation, human pluripotent stem cells were expanded under mTeSR1 feeder free conditions and enzymatic EB formation combined with stationary culture conditions was used throughout the differentiation process. The following combinations of media components were considered for differentiation studies:
VNIM+B27+N2+IGF-1
VNIM+B27+IGF-1 (no N2)
VNIM+N2+IGF-1 (no B27)
VNIM+IGF-1 (no B27 and no N2)
VNIM+IGF-1+B27 (retinoic acid free)+N2
VNIM+B27 (retinoic acid free)+IGF-1 (no N2)

Figure 17:
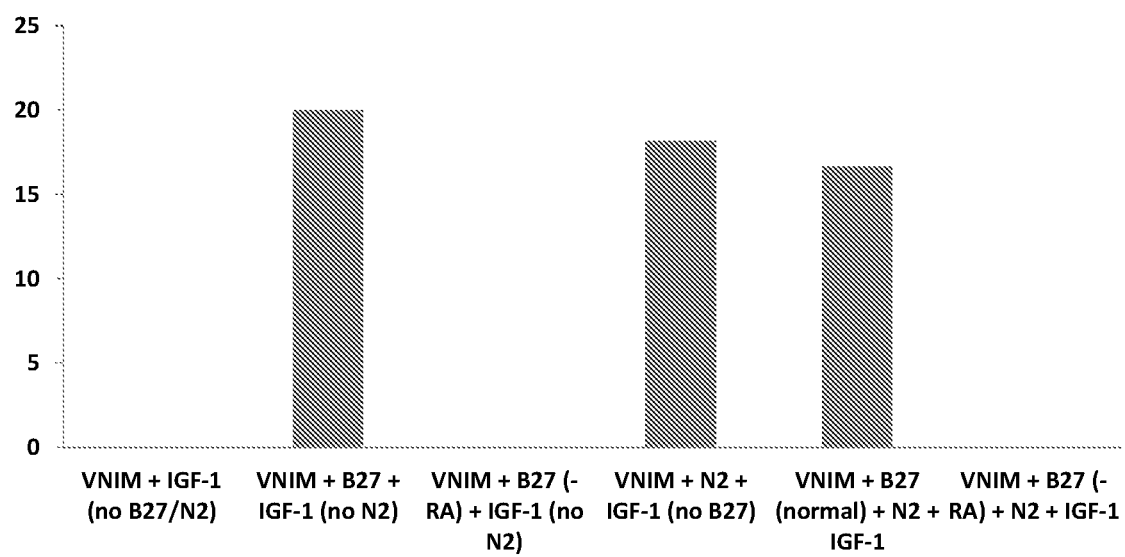
FIG. 17 shows the impact of N2 and B27 in the emergence of optic vesicles (OVs).

Given the importance of B27 and N2 in the early stages of optic vesicle formation (OV), this analysis was performed at the earliest time point of differentiation (day 15) at which OVs emerge (FIG. 17).

These studies suggest the following:

B27 (normal composition) can compensate for the lack of N2 in the culture media;

N2 can compensate for the lack of B27 in the culture media;

Lack of both B27 and N2 is detrimental and results in abrogation of OV formation; and Addition of B27 lacking RA (−RA) either alone or with N2 has a detrimental effect on OV formation.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise. Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The reader's attention is directed to all papers and documents which are filed concurrently with or previous to this specification in connection with this application and which are open to public inspection with this specification, and the contents of all such papers and documents are incorporated herein by reference.

TABLE 1

Information on the antibodies used in this study.

| Antibody | Specificity | Dilution | Supplier |
| --- | --- | --- | --- |
| anti-Bassoon | photoreceptor ribbon synapse, presynaptic terminals, co-localises with GABA and glutamate | 1:200 | StressGen PS003 |
| anti-Calbindin D-28K (Calbindin 28) | horizontal cells, cone photoreceptors (excluding S cones), On cone bipolar cells, wide field amacrine cells, large ganglion cells | 1:200 | Chemicon AB1778 |
| anti-Cytokeratin 19 (CK19) clone RCK108 | Peripheral corneal epithelium | 1:100 | Dako M088801-2 |
| anti-Crx | postmitotic photoreceptors | 1:200 | Abnova H00001406-M02 |
| anti-Crystallin, alpha B (CRYAB) | lens epithelial cells | 1:5 | Sawada et al., 1993, 2D2B6 |
| anti-HuC/D | amacrine and ganglion cells | 1:200 | Molecular Probes A21271 |
| anti-Islet1/2 | retinal ganglion cells | 1:200 | Santa Cruz Biotechnology sc-30200 |
| anti-Ki67 | nuclear expression in proliferative cells during late G1, S, G2 and M phases of the cell cycle | 1:200 | AbCam Ab15580 |
| anti-Opsin blue | S cone photoreceptors | 1:200 | Millipore AB5407 |
| anti-Opsin red/green | L/M cone photoreceptors | 1:200 | Millipore AB5405 |
| anti-Opsin (clone RetP1) | N terminal of the rhodopsin molecule on rod photoreceptor cell bodies, inner and outer segments | 1:400 | Sigma-Aldrich O4886 |
| anti-Pax6 | neural progenitors, retinal progenitors | 1:300 | Covance PRB-278P |
| anti-Post Synaptic Density Protein 95 (PSD95) | membrane-associated guanylate kinase family synaptic protein, found in inner and outer plexiform layers | 1:200 | Millipore MAB1598 |
| anti-RAX (clone 4F4) | retina and anterior neural fold homeobox; anterior neural fold, ventral diencephalon, optic vesicles, retinal progenitors | 1:100 | Sigma-Aldrich SAB1405061 |
| anti-RAX (against the N terminal) | retina and anterior neural fold homeobox | 1:200 | Aviva Systems Biology ARP31926 |
| anti-Recoverin | photoreceptors and midget cone bipolar cells | 1:300 | Chemicon AB5585 |

TABLE 1-continued

Information on the antibodies used in this study.

| Antibody | Specificity | Dilution | Supplier |
| --- | --- | --- | --- |
| anti-Rhodopsin | rod rhodopsin | 1:200 | Santa Cruz Biotechnology sc-57432 |
| anti-Sox1 | neuroectodermal tissue, lens vesicle and neural epithelium of adjacent diencephalon | 1:200 | Cell signalling technology 4194 |
| anti-Synaptophysin | presynaptic protein synaptic vesicles, expressed in photoreceptor terminals | 1:100 | Sigma-Aldrich S 5768 |
| anti-Syntaxin (clone HPC-1) | amacrine cell bodies and processes, inner plexiform layer | 1:200 | Sigma-Aldrich S 0664 |
| anti-Neuronal Class III β-Tubulin (TUJ1) | neurons, expressed in high levels in retinal ganglion cells | 1:800 | Covance MMS-435P |
| anti-Visual System Homeobox 2 (VSX2) | VSX2 protein, retinal progenitors and bipolar cells | 1:200 | Sigma-Atlas HPA003436 |

REFERENCES

1. Schwartz, S. D., Hubschman, J. P., Heilwell, G., Franco-Cardenas, V., Pan, C. K. et al. Embryonic stem cell trials for macular degeneration: a preliminary report. *The Lancet* 379 (9817), 713-20 (2012)
2. ACT Clinical Trial: Safety and Tolerability of Sub-retinal Transplantation of hESC Derived RPE (MA09-hRPE) Cells in Patients With Advanced Dry Age Related Macular Degeneration (Dry AMD). http://clinicaltrials.gov/ct2/show/NCT01344993 (2011a)
3. ACT Clinical Trial: Sub-retinal Transplantation of hESC Derived RPE (MA09-hRPE) Cells in Patients With Stargardt's Macular Dystrophy. http://clinicaltrials.gov/ct2/show/NCT01345006 (2011b)
4. ACT Clinical Trial: Safety and Tolerability of Sub-retinal Transplantation of Human Embryonic Stem Cell Derived Retinal Pigmented Epithelial (hESC-RPE) Cells in Patients With Stargardt's Macular Dystrophy (SMD). http://clinicaltrials.gov/ct2/show/NCT01469832 (2011c)
5. Lamba, D. A., Karl, M. O., Ware, C. B., Reh, T. A. Efficient generation of retinal progenitor cells from human embryonic stem cells. *Proc Natl Acad Sci USA* 103(34), 12769-74 (2006)
6. Osakada, F., Ikeda, H., Mandai, M., Wataya, T., Watanabe, K. et al. Toward the generation of rod and cone photoreceptors from mouse, monkey and human embryonic stem cells. *Nat Biotechnol* 26(2), 215-24 (2008)
7. Osakada, F., Jin, Z. B., Hirami, Y., Ikeda, H., Danjyo, T. et al. In vitro differentiation of retinal cells from human pluripotent stem cells by small-molecule induction. *J Cell Sci.* 122(17), 3169-79 (2009)
8. Hirami, Y., Osakada, F., Takahashi, K., Okita, K., Yamanaka, S. et al. Generation of retinal cells from mouse and human induced pluripotent stem cells. *Neurosci Lett* 458(3), 126-31 (2009)
9. Meyer, J. S., Shearer, R. L., Capowski, E. E., Wright, L. S., Wallace, K. A., Modeling early retinal development with human embryonic and induced pluripotent stem cells. *Proc Natl Acad Sci USA* 106(39), 16698-703 (2009)
10. Meyer, J. S., Howden, S. E., Wallace, K. A., Verhoeven, A. D., Wright, L. S. et al. Optic vesicle-like structures derived from human pluripotent stem cells facilitate a customized approach to retinal disease treatment. *Stem Cells.* 29(8), 1206-18 (2011)
11. Jin, Z. B., Okamoto, S., Osakada, F., Homma, K., Assawachananont, J. et al. Modeling retinal degeneration using patient-specific induced pluripotent stem cells. *PLoS One* 6(2), e17084 (2011)
12. Amirpour, N., Karamali, F., Rabiee, F., Rezaei, L., Esfandiari, E. et al. Differentiation of human embryonic stem cell-derived retinal progenitors into retinal cells by Sonic hedgehog and/or retinal pigmented epithelium and transplantation into the subretinal space of sodium iodate-injected rabbits. *Stem Cells Dev.* 21(1), 42-53 (2012)
13. Phillips, M. J., Wallace, K. A., Dickerson, S. J., Miller, M. J., Verhoeven, A. et al. Blood-derived Human iPS Cells Generate Optic Vesicle-like Structures with the Capacity to Form Retinal Laminae and Develop Synapses. *Invest Ophthalmol Vis Sci.* 53(4), 2007-19 (2012)
14. Mellough, C. B., Sernagor, E., Moreno-Gimeno, I., Steel, D. H., Lako, M. Efficient stage-specific differentiation of human pluripotent stem cells toward retinal photoreceptor cells. *Stem Cells.* 30(4), 673-86 (2012)
15. Nakano, T., Ando, S., Takata, N., Kawada, M., Muguruma, K. et al. Self-Formation of Optic Cups and Storable Stratified Neural Retina from Human ESCs. *Cell Stem Cell.* 10(6), 771-85 (2012)
16. Banin, E., Obolensky, A., Idelson, M., Hemo, I., Reinhardtz, E. et al. Retinal incorporation and differentiation of neural precursors derived from human embryonic stem cells. *Stem Cells.* 24(2), 246-57 (2006)
17. Lamba, D. A., Gust, J., Reh, T. A. Transplantation of human embryonic stem cell-derived photoreceptors restores some visual function in Crx-deficient mice. *Cell Stem Cell.* 4(1), 73-9 (2009)
18. Lamba, D. A., McUsic, A., Hirata, R. K., Wang, P. R., Russell, D. et al. Generation, purification and transplantation of photoreceptors derived from human induced pluripotent stem cells. *PLoS ONE.* 5(1), e8763 (2010)
19. MacLaren, R. E., Pearson, R. A., MacNeil, A., Douglas, R. H., Salt, T. E. et al. Retinal repair by transplantation of photoreceptor precursors. *Nature.* 444(7116), 203-7 (2006)
20. Lakowski, J., Baron, M., Bainbridge, J., Barber, A. C., Pearson, R. A. et al. Cone and rod photoreceptor transplantation in models of the childhood retinopathy Leber congenital amaurosis using flow-sorted Crx-positive donor cells. *Hum Mol Genet.* 19(23), 4545-59 (2010)

21. Pera, E. M., Wessely, O., Li, S. Y., De Robertis, E. M. Neural and head induction by insulin-like growth factor signals. *Dev. Cell.* 1(5), 655-65 (2001)
22. Rodrigues, M., Waldbillig, R. J., Rajagopalan, S., Hackett, J., LeRoith, D. et al. Retinal insulin receptors: localization using a polyclonal anti-insulin receptor antibody. *Brain Res.* 443(1-2), 389-94 (1988)
23. Narayanan, K., Wadhwa, S. Photoreceptor morphogenesis in the human retina: a scanning electron microscopic study. *Anat Rec.* 252(1), 133-9 (1998)
24. Nag, T. C., Wadhwa, S. Differential expression of syntaxin-1 and synaptophysin in the developing and adult human retina. *J. Biosci.* 26(2), 179-91 (2001)
25. Armstrong, L., Tilgner, K., Saretzki, G., Atkinson, S. P., Stojkovic, M. et al. Human induced pluripotent stem cell lines show stress defense mechanisms and mitochondrial regulation similar to those of human embryonic stem cells. *Stem Cells.* 28(4), 661-73 (2010)
26. Jiang, Y., Cowley, S. A., Siler, U., Melguizo, D., Tilgner, K. et al. Derivation and functional analysis of patient-specific induced pluripotent stem cells as an in vitro model of chronic granulomatous disease. *Stem Cells.* 30(4), 599-611 (2012)

a) L-glutamine;
b) B27 supplement; and
c) insulin-like growth factor (IGF-1),
iii) subsequently differentiating the EB culture of step ii) in suspension culture for a second time period in a second neural cell culture medium comprising:
a) L-glutamine;
b) B27 supplement;
c) N2 supplement; and
d) IGF-1,
wherein said synthetic retina contains laminated retinal tissue comprising apically positioned photoreceptors and basally located ganglion cells.

2. The method of claim 1, wherein at least one of said first neural cell culture medium and said second neural cell culture medium further comprises Dulbecco's Modified Eagle Medium (DMEM), Nutrient Mixture F-12 (F-12), or a combination thereof.

3. The method of claim 1, wherein at least one of said first neural cell culture medium and said second neural cell culture medium further comprises non-essential amino acid (NAA).

The invention claimed is:

1. A method of producing a synthetic retina in 3D culture conditions throughout, the method comprising:
    i) providing an embryoid body (EB),
    ii) differentiating the EB in suspension culture for a first time period in a first neural cell culture medium comprising:

4. The method of claim 1, wherein said first neural cell culture medium further comprises Knockout serum replacement (KOSR).

5. A method of producing a synthetic retina in 3D culture conditions throughout, the method comprising:

i) providing an embryoid body (EB);
ii) differentiating the EB in suspension culture for a first time period in a first neural cell culture medium comprising IGF-1;
iii) subsequently differentiating the EB in suspension culture for a second time period in a second neural cell culture medium comprising IGF-1, wherein said synthetic retina contains laminated retinal tissue comprising apically positioned photoreceptors and basally located ganglion cells, and wherein said first and second neural cell culture medium do not comprise each of recombinant mouse Noggin (rmNoggin), recombinant human Dickkopf-1 (Dkk1), recombinant human Lefty A (rh Lefty A), Human Sonic Hedgehog (Shh), 3,3',5-triiodo-L-thyronine (T3), recombinant human Basic Fibroblast Growth Factor (rhbFGF), retinoic acid, taurine and Human Activin-A.

6. The method of claim 5, wherein said first neural cell culture medium further comprises:
   i) B27 supplement;
   ii) L-glutamine;
   iii) Knockout serum replacement (KOSR); or
   iv) any combination of the above.

7. The method of claim 5, wherein said second neural cell culture medium further comprises:
   i) B27 supplement;
   ii) L-glutamine;
   iii) N-2 supplement; or
   iv) any combination of the above.

8. The method according to claim 1, wherein said first time period is from about 30 to about 40 days.

9. The method according to claim 1, wherein said first time period is about 37 days.

10. The method according to claim 1, wherein said second time period is from about 30 to about 60 days.

11. The method according to claim 1, wherein said second time period is about 53 days.

12. The method according to claim 1, wherein said IGF-1 is the human IGF-1 of SEQ ID NO: 1.

13. The method according to claim 12, wherein said human IGF-1 is a recombinant human IGF-1.

14. The method according to claim 1, further comprising a step of isolating said synthetic retina from said second neural cell culture medium.

15. A synthetic retina obtained by the method of claim 1.

16. A pharmaceutical composition comprising the synthetic retina according to claim 15.

17. A method of identifying agents for treating a retinal disease, the method comprising: i) providing a synthetic retina obtained by the method of claim 1; ii) contacting an agent with the synthetic retina; iii) monitoring the viability or degeneration of retinal cells in the synthetic retina; iv) comparing the viability or degeneration of the retinal cells in the synthetic retina in the presence of the agent with the viability or degeneration of the retinal cells in the absence of the agent; and v) identifying the agent as an agent for treating a retinal disease if the agent increases the viability of the retinal cells in the synthetic retina as compared to the viability of the retinal cells in the absence of the agent.

18. The method of claim 1, wherein said first neural cell culture medium further comprises Knockout serum replacement (KOSR) wherein the amount of KOSR is reduced during the first time period.

19. The method of claim 5, wherein said first neural cell culture medium further comprises:
   i) B27 supplement;
   ii) L-glutamine;
   iii) Knockout serum replacement (KOSR), wherein the amount of KOSR in the first neural culture cell medium is reduced during the first-time period; or
   iv) any combination of the above.

20. A method of identifying agents for treating a neurological disease, the method comprising: i) providing a synthetic retina obtained by the method of claim 1; ii) contacting an agent with the synthetic retina; iii) monitoring the viability or degeneration of retinal cells in the synthetic retina; iv) comparing the viability or degeneration of the retinal cells in the synthetic retina in the presence of the agent with the viability or degeneration of the retinal cells in the absence of the agent; and v) identifying the agent as an agent for treating a neurological disease if the agent increases the viability of the retinal cells in the synthetic retina as compared to the viability of the retinal cells in the absence of the agent.

* * * * *